US009127315B2

(12) United States Patent
Bontrop et al.

(10) Patent No.: US 9,127,315 B2
(45) Date of Patent: Sep. 8, 2015

(54) MEANS AND METHODS FOR HAPLOTYPING MHC-DRB LOCI IN MAMMALS AND USES THEREOF

(75) Inventors: Ronald Edward Bontrop, Voorschoten (NL); Gabriele Gerda Maria Doxiadis, Leiden (NL)

(73) Assignee: STICHTING BIOMEDICAL PRIMATE RESEARCH CENTRE, Rijswijk (NL)

( * ) Notice: Subject to any disclaimer, the term of this patent is extended or adjusted under 35 U.S.C. 154(b) by 963 days.

(21) Appl. No.: 12/595,292

(22) PCT Filed: Apr. 10, 2008

(86) PCT No.: PCT/NL2008/050199
§ 371 (c)(1),
(2), (4) Date: Jan. 7, 2010

(87) PCT Pub. No.: WO2008/123777
PCT Pub. Date: Oct. 16, 2008

(65) Prior Publication Data
US 2010/0112580 A1 May 6, 2010

(30) Foreign Application Priority Data

Apr. 10, 2007 (EP) ..................................... 07105879
May 1, 2007 (EP) ..................................... 07107288

(51) Int. Cl.
| C12Q 1/68 | (2006.01) |
| C12P 19/34 | (2006.01) |
| C07H 21/02 | (2006.01) |
| C07H 21/04 | (2006.01) |

(52) U.S. Cl.
CPC ................................... *C12Q 1/6881* (2013.01)

(58) Field of Classification Search
CPC .................................................... C12Q 1/6881
See application file for complete search history.

(56) References Cited

U.S. PATENT DOCUMENTS

| 5,908,749 A | 6/1999 | Mignot et al. |
| 2003/0108940 A1 | 6/2003 | Inoko et al. |

FOREIGN PATENT DOCUMENTS

| EP | 0414469 B1 | 10/1996 |
| WO | 2008123777 A1 | 4/2010 |

OTHER PUBLICATIONS

Arnold R. et al. Gene (2000) vol. 253, pp. 209-214.*
van Haeringen et al. Animal Genetics (1999) vol. 30, pp. 169-176.*
STS Marker D6S2878 from http://genome.csdb.cn, pp. 1-3 printed on Aug. 25, 2014.*
Giraldo-Vela et al., "The Major Histocompatibility Complex Class II Alleles Mamu-DRB1*1003 and -DRB1*0306 Are Enriched in a Cohort of Simian Immunodeficiency Virus-Infected Rhesus Macaque Elite Controllers", Journal of Virology, vol. 82, No. 2, pp. 859-870; 2008.
Bergstrom et al., "Tracing the Origin of HLA-RB1 Alleles by Microsatellite Polymorphism", American Journal of Human Genetics, vol. 64, pp. 1709-1718; 1999.
Doxiasis et al., "A Highly Divergent Microsatellite Facilitating Fast and Accurate DRB Haplotyping in Human and Rhesus Macaques", PNAS, vol. 104, No. 21, pp. 8907-8912; 2007.
Epplen et al., "Coding Versus Intron Variability: Extremely Polymorphic HLA-DRB1 Exons are Flanked by Specific Composite Microsatellites, Even in Distant Populations", Human Genetics, vol. 99, pp. 399-406; 1997.
Slierendregt et al., "Identification of an MHC-DPB1 Allele Involved in Susceptibility to EAE (Experimental Autoimmune Encephalomyelitis) in Rhesus Macques", International Immunology, vol. 7, pp. 1671-1679; 1995.
Bontrop et al., "Evolution of Major Histocompatibility Complex Polymorphisms and T-Cell Receptor Diversity in Primates", Immunology Rev., vol. 143, pp. 33-62; 1995.
Klein et al., "Nomenclature for the Major Histocompatibility Complexes of Different Species: a Proposal", Immunogenetics, vol. 31, pp. 217-219; 1990.
Bodmer et al., "Nomenclature for Factors of the HLA System, 1998", European Journal of Immunogenetics, vol. 26, pp. 81-116; 1999.
Pociot et al., "Genetics of Type 1 Diabetes Mellitus", Genes and Immunity, vol. 3, pp. 235-249; 2002.
Doxiadis et al., "Extensive Sharing of MHC Class II Alleles Between Rhesus and Cynomolgus Macaques", Immunogenetics, vol. 58, pp. 259-268; 2006.
Penedo et al., "Microsatellite Typing of the Rhesus Macaque MHC Region", Immunogenetics, vol. 57, pp. 198-209; 2005.
Jin et al., "Mutation Rate Varies Among Alleles at a Microsatellite Locus: Phylogenetic Evidence", Proc. Natl. Acad. Sci., vol. 93, pp. 15285-15288; 1996.
Maueler et al., "The (gt)n(ga)m Containing Intron 2 of HLA-DRB Alleles Binds a Zinc-Dependent Protein and Forms non B-DNA Structures", Gene, vol. 226, pp. 9-23; 1999.
Vowles et al., "Evidence of Widespread Convergent Evolution Around Human Microsatellites", PLoS Biology, vol. 2, pp. 1157-1167; 2004.
de Groot et al., "Genetic Makeup of the DR Region in Rhesus Macaques: Gene Content, Transcripts, and Pseudogenes", The Journal of Immunology, pp. 6152-6157; 2004.
Schreuder et al., The HLA Dictionary 2004: a Summary of HLA-A, -B, -C, -DRB1/3/4/5 and -DQB1 Alleles and Their Association with Serologically Defined HLA-A, -B, -C, -DR and -DQ Antigens, Tissue Antigens, vol. 65, pp. 1-55; 2005.
Rieβ et al., "Hypervariability of Intronic Simple (gt)n (ga)m Repeats in HLA-DRB Genes", Immunogenetics, vol. 32, pp. 110-116; 1990.

(Continued)

*Primary Examiner* — Stephen Kapushoc
(74) *Attorney, Agent, or Firm* — Hoffmann & Baron, LLP

(57) ABSTRACT

The invention relates to the typing of MHC-DRB loci in mammals. In particular, the invention provides a typing procedure for the mammalian DRB region that allows an easy, economical, high resolution, fast and accurate haplotyping protocol. The invention further provides the use of said typing procedure in genetic applications, and provides a kit for typing of MHC-DRB loci.

9 Claims, 13 Drawing Sheets

(56) References Cited

OTHER PUBLICATIONS

Kriener et al., "Convergent Evolution of Major Histocompatibility Complex Molecules in Humans and New World Monkeys", Immunogenetics, vol. 51, pp. 169-178; 2000.

Trtkova et al., "Mhc-DRB Genes and the Origin of New World Monkeys", Molecular Phylogenetics and Evolution, vol. 4, No. 4, pp. 404-419; 1995.

Petes et al., "Stabilization of Microsatellite Sequences by Variant Repeats in the Yeast *Saccharomyces cerevisiae*", Genetics, vol. 146, pp. 491-498; 1997.

Wierdl et al., "Microsatellite Instability in Yeast Dependence on the Length of the Microsatellite", Genetics, vol. 146, pp. 769-779; 1997.

Ammer et al., "Exonic Polymorphism vs Intronic Simple Repeat Hypervariablity in MHC-DRB Genes", Immunogenetics, vol. 35, pp. 332-340; 1992.

Andersson et al., "Class II Genes of the Human Major Histocompatibility Complex", The Journal of Biological Chemistry, vol. 262, No. 18, pp. 8748-8758; 1987.

Outteridge et al., "The PCR Typing of MHC-DRB Genes in the Sheep Using Primers for an Intronic Microsatellite; Application to Nematode Parasite Resistance", Immunology and Cell Biology, vol. 74, pp. 330-336; 1996.

Al-Harbi et al., Specific HLA-DRB and -DQB Alleles and Hapolytes Confer Disease Susceptibility or Resistance in Bahraini Type I Diabetes Patients, Clinical and Diagnostic Laboratory Immunology, vol. 11, No. 2, pp. 292-296; 2004.

Almawi et al., "Distribution of HLA Class II (DRB1/DQB1) Alleles and Haplotypes Among Bahraini and Lebanese Arabs", Transplantation Proceedings, vol. 36, pp. 1844-1846; 2004.

Bak et al., "Identification and Analysis of MHC Class II DRB1 (Patr-DRB1) Alleles in Chimpanzees", Tissue Antigens, vol. 67, pp. 134-142; 2006.

Carrington et al., "Microsatellite Markers in Complex Disease: Mapping Disease-Associated Regions Within the Human Major Histocompatibility Complex", Microsatellites Evolution and Applications, pp. 225-237; 1999.

Cavestro et al., "Association of HLA-DRB1*0401 Allele with Chronic Pancreatitis", Pancreas, vol. 26, pp. 388-391; 2003.

Dyment et. al., "Genetics of Multiple Sclerosis", Lancet Neurology, vol. 3, pp. 104-110; 2004.

Dyment et al., "Complex Interactions Among MHC Haplotypes in Multiple Sclerosis: Susceptibility and Resistance", Human Molecular Genetics, vol. 14, No. 14, pp. 2019-2026; 2005.

Erlich et al., "HLA DR-DQ Haplotypes and Genotypes and Type 1 Diabetes Risk", Diabetes, vol. 57, pp. 1084-1092; 2008.

Fogdell et al., "The Multiple Sclerosis- and Narcolepsy- Associated HLA Class II Haplotype Includes the DRB5*0101 Allele", Tissue Antigens, vol. 46, pp. 333-336; 1995.

Fries et al., "HLA-DRB1 Genotype Associations in 793 White Patients from a Rheumatoid Arthritis Inception Cohort", Arthritis & Rheumatism, vol. 46, No. 9, pp. 2320-2329; 2002.

Gombos et al., "Analysis of Extended Human Leukocyte Antigen Haplotype Association with Addison's Disease in Three Populations", European Journal of Endocrinology, vol. 157, pp. 757-761; 2007.

Graham et al., "Specific Combinations of HLA-DR2 and DR3 Class II Haplotypes Contribute Graded Risk for Disease Susceptibility and Autoantibodies in Human SLE", European Journal of Human Genetics, vol. 15, pp. 823-830; 2007.

Gregersen et al., "Functional Epistatis on a Common MHC Haplotype Associated with Multiple Sclerosis", Nature, vol. 443, pp. 574-547; 2006.

Planelles et al., "HLA-DQA, -DQB and -DRB Allele Contribution to Narcolepsy Susceptibility", European Journal of Immunogenetics, vol. 24, pp. 409-421; 1997.

Prat et al., "HLA-DRB5*0101 and -DRB1*1501 Expression in the Multiple Sclerosis-Associated HLA-DR15 Haplotype", Journal of Neuroimmunology, vol. 167, pp. 108-119; 2005.

Ramagopalan et al., "The Inheritance of Resistance Alleles in Multiple Sclerosis", PLoS Genetics, vol. 3, pp. 1607-1613; 2007.

Sasaki et al., "New HLA DRB1 and DQB1 Haplotypes in a Pedigree of Familial Graves' Disease in Japan", Endocrine Journal, vol. 54, No. 5, pp. 721-725; 2007.

Shiina et al., "An Update of the HLA Genomic Region, Locus Information and Disease Associations: 2004", Tissue Antigens, vol. 64, pp. 631-649; 2004.

Zavattari et al., "Conditional Linkage Disequilibrium Analysis of a Complex Disease Superlocus, IDDM1 in the HLA Region, Reveals the Presence of Independent Modifying Gene Effects Influencing the Type 1 Diabetes Risk Encoded by the Major HLA-DQB1, -DRB1 Disease Loci", Human Molecular Genetics, vol. 10, No. 8, pp. 881-889; 2001.

Kanazawa et al., "Aberrant MHC Class II Expression in Mouse Joints Leads to Arthritis with Extraarticular manifestations Similar to Rheumatoid Arthritis", PNAS, vol. 103, No. 39, pp. 14465-14470; 2006.

Aoki et al., NOD Mice Autoimmunity, Autoimmunity Reviews, vol. 4, pp. 373-379; 2005.

Slierendregt et al., "Expansion and Contraction of Rheus Macaque DRB Regions by Duplication and Deletion", Journal of Immunology, vol. 152, pp. 2298-2307; 1994.

Robinson et al., "IMGT/HLA and IMGT/MHC: Sequence Databases for the Study of the Major Histocompatibility Complex", Nucleic Acids Research, vol. 31, No. 1, pp. 311-314; 2003.

Doxiadis et al., "Unprecedented Polymorphism of Mhc-DRB Region Configurations in Rhesus Macaques", Journal of Immunology, vol. 164, pp. 3193-3199; 2000.

Doxiadis et al., "Differential Evolutionary MHC Class II Strategies in Humans and Rhesus Macaques: Relevance for Biomedical Studies", Immunological Reviews, vol. 183, pp. 76-85; 2001.

\* cited by examiner

MEANS AND METHODS FOR HAPLOTYPING MHC-DRB LOCI IN MAMMALS AND USES THEREOF

This application is the U.S. National Phase of, and Applicants claim priority from, International Application Number PCT/NL2008/050199 filed 10 Apr. 2008, European Patent Application No. 07105879.6 filed 10 Apr. 2007 and European Patent Application No. 07107288.8 filed 1 May 2007, each of which are incorporated herein by reference.

BACKGROUND OF THE INVENTION

The invention relates to the field of biology and medicine. In particular, the invention relates to the typing of MHC-DRB loci in mammals.

The Major Histocompatibility Complex (MHC) is a large genomic region that is present in most vertebrates, although individual MHC region-linked genes have been identified in invertebrate genomes such as *Drosophila melanogaster* and *Caenorhabditis elegans*. The MHC gene products play a key role in adaptive immunology. Genes of the MHC are among the most polymorphic loci known in vertebrates, due to a high rate of mutation and recombination. Major differences between species reside not only in the number and identity of MHC genes, but also in the degree of allelic polymorphism for individual genes.

In general, three subgroups of MHC molecules can be defined, termed class I, II and III gene products. Molecules encoded by the so-called classical MHC class I and class II genes, present short peptides derived from proteins of pathogens and self antigens to the immune system. MHC class I genes encode molecules that are present on the surfaces of nearly all nucleated cells. These gene products are mainly responsible for facilitating immune responses to intracellularly processed pathogens such as viruses. MHC class II gene products are mainly present in a subset of antigen-presenting cells such as B-lymphocytes and activated T-lymphocytes. Class II gene products are primarily involved in the immune response against extracellular pathogens such as bacteria. Furthermore, they play an important role in recognition of foreign and self-antigens. MHC class III gene products are not involved in antigen presentation but rather represent other immune-related components such as components of the complement system.

Of particular importance are the MHC genes that encode the cell surface, antigen-presenting molecules. In humans, these genes are referred to as Human Leukocyte Antigen (HLA) genes. The classical MHC genes HLA-A, HLA-B, and HLA-C belong to MHC class I, encoding the alpha chain of the respective MHC molecule. The HLA class II region is divided into -DP, -DQ, and -DR. The classical HLA-DR, -DQ, and -DP molecules are transmembrane heterodimers, composed of an alpha- and beta-chain subunit encoded by the A and B genes, respectively.

Defects in some MHC class II genes have been associated with autoimmune disorders such as arthritis and diabetes (Otsuka et al. 2006. Proc Natl. Acad Sci USA. 103: 14465-7; Aoki et al. 2005. Autoimmun Rev. 4: 373-9). Similarly, polymorphisms in MHC class II genes have been associated with susceptibility to a range of infectious diseases including malaria, tuberculosis, leprosy, typhoid fever, hepatitis and HIV/AIDS. For instance, experimental autoimmune encephalomyelitis in rhesus macaques, a model for the human disease multiple sclerosis, is known to be influenced by certain MHC class II alleles (Slierendrecht et al. 1995. International Immunology, Vol. 7: 1671-1679).

In the human population, five major -DRB region configurations are classified. These region configurations share an invariant HLA-DRA gene and a -DRB9 gene segment but differ in physical length and also in the composition and number of other DRB loci. Like humans, other primates such as chimpanzees, gorillas, and rhesus macaques have variable numbers of MHC-DRB loci per haplotype (Doxiadis et al. 2000. J. of Immunol. 164: 3193-3199). For example, the DRB region configuration in rhesus macaques (Macaca mulatta), termed Mamu-DRB, is highly plastic and has been subject to various contractions and expansions (Slierendregt et al. 1994. J Immunol 152: 2298-307). In humans a high degree of polymorphism is observed for the DRB1 locus present on all haplotypes (Robinson et al. 2003. Nucleic Acids Res 31: 311-4). In rhesus macaques, however, a high degree of region configuration polymorphism has been described characterized by marked differences with regard to number and content of distinct loci present per haplotype (Doxiadis et al. 2000. J Immunol 164: 3193-9; Doxiadis et al. 2001. Immunol Rev 183: 76-85). The Mamu-DRB region configurations themselves, however, display a relatively low degree of polymorphism. Most of the Mamu-DRB alleles belong to loci/lineages that are shared with humans (Bontrop et al. 1999. Immunol Rev 167: 339-50), and their alleles have been named accordingly (Klein et al. 1990. Immunogenetics 31: 217-9). Similar observations regarding sharing of certain MHC-DRB loci/lineages with human orthologues have been made for other primate species, whereas DRB alleles are mostly species specific (Bontrop et al. 1999. Immunol Rev 167: 339-50).

It is generally accepted that allelic polymorphisms of the MHC class II genes warrant that different allotypes select distinct peptides for T cell activation, preventing one particular pathogen from sweeping through an entire population. Most sequence variability is confined to exon 2 of the MHC-DPB, -DQA, -DQB, and -DRB genes. One of the most polymorphic regions in humans is the HLA-DRB region with more than 500 alleles described worldwide until now (Bodmer et al. 1999. Eur J. Immunogenet. 26: 81). In rhesus macaques, a species far less analysed than humans, already more than 135 Mamu-DRB distinct genes/alleles have been determined, a number which will increase rapidly when more animals are analysed.

Due to the complexity of the DRB-region, the existing typing procedures, involving single-strand conformation polymorphism, denaturing gradient gel electrophoresis (DGGE), restriction fragment length polymorphism analyses, or sequence analyses, are cumbersome and time consuming. It is therefore an object of the present invention to provide a typing procedure for the mammalian DRB region that allows an easy, economical, high resolution, fast and accurate haplotyping protocol.

BRIEF DESCRIPTION OF DRAWINGS

FIG. 1: HLA-DRB exon 2 sequences subjected to phylogenetic analyses, on which D6S2878 sequences have been superimposed.

DESCRIPTION OF THE INVENTION

Figure 2:
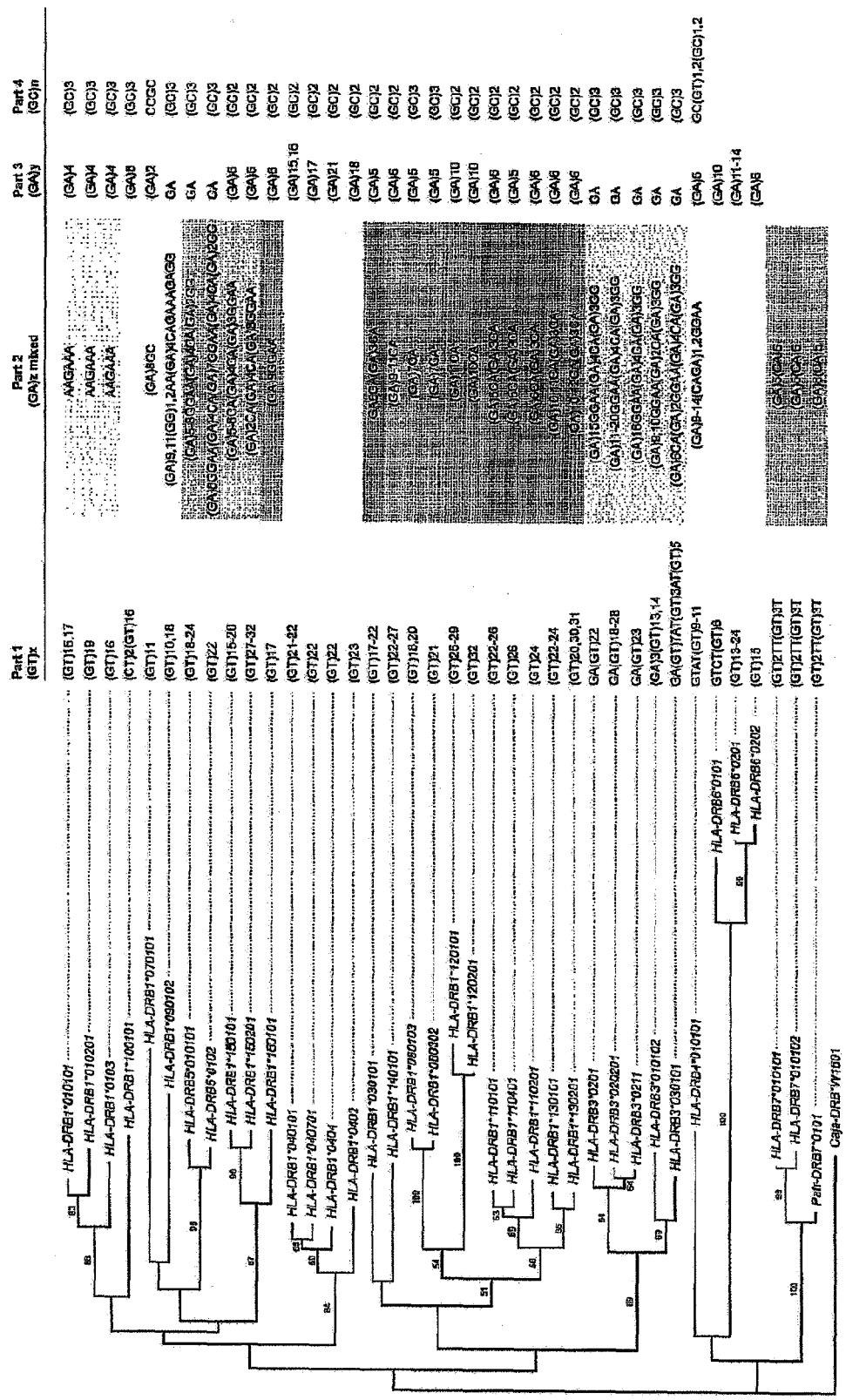
FIG. 2: Mamu-DRB exon 2 sequences subjected to phylogenetic analyses, on which D6S2878 sequences have been superimposed.

Therefore, in one aspect the present invention provides a method for determining a DRB haplotype in a sample comprising nucleic acid from a mammalian cell, said method comprising amplifying at least an intron 2 microsatellite-containing part of at least one DRB-gene from said nucleic acid; determining the type of intron 2 microsatellite present in said at least one DRB-gene; and determining the DRB haplotype of said cell from said type of intron 2 microsatellite present in said at least one DRB-gene.

The inventors have established that the type of intron 2 microsatellite present in said at least one DRB-gene is indicative of the DRB-allele that is associated with said intron in a cis-configuration, thus allowing the identification of said DRB-allele by typing of the associated intron 2 microsatellite. An advantage of said method is that the typing of said intron 2 microsatellite can be performed by relatively simple methods which do not involve complicated methods such as single-strand conformation polymorphism or sequence analyses. Therefore, said method provides an easy and economical method for determining a DRB haplotype in a sample.

A complex dinucleotide repeat or microsatellite, D6S2878, is located in the beginning of intron 2 of the DRB genes of human and non-human primates (Bergstroem et al. 1999. Am J Hum Genet 64: 1709-1718; Epplen et al. 1997. Hum Genet 99: 399-406; Riess et al. 1990. Immunogenetics 32:110-116). This microsatellite displays a complex polymorphism profile concerning repeat length variability as well as sequence variation. According to the present invention, the variability of said microsatellite can be used for typing of the cis-associated DRB-allele. The number of and identity of distinct DRB-alleles that are present in a sample, as determined by the number and types of intron 2 microsatellites that are present in said sample, is used to determine a DRB-haplotype.

The number and types of intron 2 microsatellites that are present in a sample can be determined by any method known in the art, including but not limited to sequence analyses and sequence-specific amplification. However, a quick and convenient method for determining the number and types of intron 2 microsatellites comprises the determination of the length of the microsatellite, as it was found that the length of the intron 2 microsatellite is indicative for the cis-associated DRB-allele.

Therefore, in a preferred embodiment the invention provides a method for determining a DRB haplotype, wherein the typing of the intron 2 microsatellite is based on the length of said microsatellite.

Thus, a DRB-haplotype can be determined by analysis of the length of intron 2 microsatellite that is present in the amplified fragments from the at least one DRB gene. Each haplotype is identified by a specific number and size of the amplified fragments. Thus by identifying the specific number and size of the amplified fragments, the haplotype can be identified.

The number of distinct fragments obtained after amplification will depend on the number of distinct DRB-alleles that are present in a particular DRB-haplotype. The total number of DRB-alleles that can be present in a sample, and consequently resulting in multiple distinct amplified fragments, also depends on whether the cell is homozygous or heterozygous for a DRB-haplotype, as in the latter case more distinct fragments might be present.

In a preferred embodiment, the type of DRB-allele is determined by comparing the amplified intron 2 microsatellite-derived fragments with a reference. Said reference can be a sample from a individual of which the types of DRB-alleles and the corresponding DRB-haplotype have been previously determined. Said reference can, for example, be taken along in the amplification reaction. The reference sample can be taken from the same or a different species, however, it is preferred that said reference sample is taken from the same species.

Therefore, the invention also provides a method wherein a DRB haplotype is determined by comparing the detected types of intron 2 microsatellite with a reference.

In preferred embodiment, said reference is taken from a sample from an individual of which the types of DRB-genes and the corresponding DRB-haplotype have been previously determined and of which relevant data, comprising number and length and/or sequence of the amplified intron 2 microsatellite fragments, have been stored in a database.

Therefore, in this embodiment, the invention provides a method wherein a type of intron 2 microsatellite is determined by comparing with a reference comprising a database of DRB haplotypes correlated with the associated intron 2 microsatellite types.

In a preferred embodiment, a database according to the invention is present in an electronic storage device, such as, but not limited to, a computer or a server. It is further preferred that said database comprising said reference can be addressed to compare the amplified intron 2 microsatellite-derived fragments with said reference.

Amplification of at least intron 2, or a microsatellite-containing portion thereof, of a DRB-gene can be performed by any method known in the art including, but not limited to, polymerase chain reaction, strand displacement amplification, nucleic acid sequence-based amplification, rolling circle amplification technology, and transcription-mediated amplification. Each of these amplification methods uses different approaches to achieve the amplification of nucleic acid molecules to amounts that can subsequently be detected.

In a preferred embodiment, the invention also provides a primer pair that spans the region containing said intron 2 microsatellite, for amplifying at least said intron 2 microsatellite-containing part of at least one DRB-gene.

According to this embodiment, said primer pair is preferably selected to allow amplification of at least 1 DRB gene, more preferred at least 2 DRB genes, more preferred at least 3 DRB genes, more preferred at least 4 DRB genes, more preferred at least 5 DRB genes, more preferred at least 6 DRB genes, more preferred at least 7 DRB genes, more preferred at least 10 DRB genes, that are present within the DRB region of one or more individuals of a species.

Therefore, each of the primers of said primer pair preferably is selected to hybridize to a nucleic acid region that is conserved in most or essentially all DRB-genes and alleles thereof within a species, thereby allowing the amplification of said intron 2 microsatellite of essentially all DRB genes and alleles thereof that are present within the DRB region of one or more individuals of a species.

In a preferred embodiment, said primer pair comprises a first primer of which the nucleotide sequences corresponds to a conserved nucleotide sequence that is present in a position that is adjacent to the microsatellite in intron 2, and a second primer of which the nucleotide sequences corresponds to a conserved sequence that is present on the opposite side of said microsatellite sequence, relative to the first primer.

In a preferred embodiment, said first primer is selected from a region spanning the 3' end of exon 2 and the 5' start of intron 2 of a DRB gene. This region was found to be conserved within species, but not between species. A second primer can be selected from a region comprising a conserved sequence, said region being present within a range of up to 1000 nucleotides from the microsatellite at the opposite side of the microsatellite in intron 2 of a DRB gene relative to said first primer.

In a more preferred embodiment, said second primer is selected from a region comprising conserved sequences that are present within a range of 5 to 60 nucleotides from the microsatellite at the opposite side of the microsatellite in intron 2 of a DRB gene, relative to said one primer.

Therefore, in an even further preferred embodiment, a primer pair according to the invention comprises a first primer of which the nucleotide sequences corresponds to a conserved region spanning the 3' end of exon 2 and the 5' start of intron 2 of a DRB gene, and a second primer of which the nucleotide sequences corresponds to a region comprising conserved sequences that is present within a range of 5 to 60 nucleotides from the microsatellite at the opposite side of the microsatellite in intron 2 of a DRB gene, relative to said first primer.

In yet an even further preferred embodiment, said first primer is chosen from the primers

```
GAGAGCTTCACAGTGCAGC;         (SEQ ID NO 1)

TTCACAGTGCAGCGGCGAGGT;       (SEQ ID NO 2)
and

CGTGTCCCCACAGCACGTTTC        (SEQ ID NO 6)
``` and said second primer is chosen from the primers

```
GAGAGGATTCTAAATGCTCAC;       (SEQ ID NO 3)

ACACCTGTGCCCTCAGAACT;        (SEQ ID NO 4)
and

ACATCTGTGTCCTCAGACCT.        (SEQ ID NO 5)
```

It is furthermore preferred that the amplified nucleic acid molecules comprising at least intron 2 of a DRB gene, or a microsatellite-containing portion thereof that are derived from different DRB-alleles can be discriminated by physical characteristics such as size, isoelectric point, or nucleotide sequence of the molecules. Therefore, the length of the amplified fragment is preferably less than 1000 nucleotides, more preferred less than 900 nucleotides, more preferred less than 800 nucleotides, more preferred less than 700 nucleotides, more preferred less than 600 nucleotides, more preferred less than 500 nucleotides, more preferred less than 400 nucleotides, more preferred less than 300 nucleotides.

An amplified fragment comprising the microsatellite can be detected by any method known in the art. Detection methods include real-time detection methods such as DNA binding fluorophores, 5' endonuclease, adjacent linear and hairpin oligoprobes, and self-fluorescing amplicons.

In another embodiment, detection of the amplified nucleic acid is performed by post-amplification methods, including but not limited to, colorimetric detection, chemiluminescence, and gel electrophoresis detection.

Gel electrophoresis comprises the analysis of nucleic acid molecules by using a polymer such as agarose or polyacrylamide. Known methods include slab gel electrophoresis and capillary gel electrophoresis. Nucleic acid molecules are separated on the polymer based on physical characteristics such as size, shape, or isoelectric point, of the molecules. Visualization of nucleic acid molecules after electrophoreses comprises classic staining procedures, including but not limited to ethidium bromide, silver, SYBR Green (2-[N-(3-dimethylaminopropyl)-N-propylamino]-4-[2,3-dihydro-3-methyl-(benzo-1,3-thiazol-2-yl)-methylidene]-1-phenyl-quinolinium; Invitrogen), coomassie blue dyes, or inorganic microparticle labels such as nanocrystals or quantum dots.

The length of an amplified nucleic acid can be determined by methods known to a skilled person, including but not limited to comparison to a known standard provided by fragments of known length, measuring of the time that is required to reach a defined position on the gel under standard conditions, and by any other method that determines the size, shape, or isoelectric point of the nucleic acid, such as mass spectrometry.

Sequence analyses of each of the amplified nucleic acid molecules, or of a suitable part thereof, can be performed using methods that are known in the art, including but not limited to, chemical analyses, enzymatic analyses using nucleotide analogues, and hybridization methods.

In a preferred embodiment, amplified nucleic acid molecules according to the invention are generated using labelled nucleotide analogues in the amplification reaction, allowing detection of said amplified nucleic acid molecules after gel electrophoresis without staining and washing procedures. Labelled nucleotide analogues that can be used include, but are not limited to, fluorescently-labelled nucleotide analogues such as cyanine-dyes (Cy3 or Cy5)-labelled analogues, and radioactively labelled nucleotide analogues.

In an alternative embodiment, amplified nucleic acid molecules are detected through the native fluorescence of nucleic acid molecules.

In a more preferred embodiment, the nucleic acid molecules are fluorescently labelled. They can be detected using any method known in the art, such as, for example, laser-induced fluorescence. Detection is based on the excitation and emission spectra of the fluorescent label that is used.

In an even more preferred embodiment, the amplified nucleic acid molecules are generated using at least one primer that is labelled. Said at least one primer can be labelled with, for example, luminescent method system such as lanthanide ions, or fluorescence-based dyes such as 6-FAM, HEX, NED, ROX, 5-FAM, JOE, Cy3, and Cy5. The use of at least one primer that is labelled will also allow detection of the amplified nucleic acid molecules by gel electrophoresis without staining and washing procedures.

Therefore, a preferred method according to the invention comprises amplifying at least an intron 2 microsatellite-containing part from a DRB gene with a primer pair, wherein one or more of the primers is labelled.

Said sample comprising nucleic acid molecules of the cell that is used for amplifying at least intron 2, or a microsatellite-containing portion thereof, may comprise any nucleic acid molecule that comprises intron 2, or at least a microsatellite-containing portion thereof. These nucleic acid molecules include, but are not limited to, unspliced RNA, such as, for example, nuclear RNA, and genomic DNA.

In a preferred embodiment, the invention provides a method for determining a DRB haplotype in a sample comprising genomic DNA.

The sample can be derived from any mammal that comprises a microsatellite in intron 2 of a DRB gene. The present invention is suitable for designing breeding programs such as used in animal husbandry and for endangered species such as whales and elephants. Non-limiting examples of a mammal comprise pets such as dog and cat; ungulates including sheep, goat, and cattle such as cow; horse; and primates.

In a preferred embodiment, the sample is derived from any human or non-human primate that comprises a microsatellite in intron 2 of a DRB gene. Not limiting examples of human or non-human primates include apes such as chimpanzee, gorilla, gibbon, siamang, orangutan, and human, Old World monkeys such as mandrill, macaque and baboon, New World monkeys, and Prosimians.

In a further preferred embodiment, a method according to the invention provides determining a DRB-haplotype in a sample that is derived from a human.

In another aspect, the invention relates to a kit for determining a DRB haplotype in a cell, said kit comprising means for amplifying at least an intron 2 microsatellite-containing part of at least one DRB-gene.

In one embodiment, said kit comprises a pair of primers that span a region of a DRB gene flanking the intron 2 microsatellite-containing part of at least one DRB-gene.

In a preferred embodiment, a first primer of said primer pair comprises sequences selected from a conserved region spanning the 3' end of exon 2 and the 5' start of intron 2 of a DRB gene, while a second primer comprises sequences selected from a conserved region that is present on the opposite side of said microsatellite sequence, relative to the first primer.

In a further preferred embodiment, said first and second primers are selected such that the length of the amplified fragment from the intron-2 of a DRB-gene is less than 1000 nucleotides, more preferred less than 900 nucleotides, more preferred less than 800 nucleotides, more preferred less than 700 nucleotides, more preferred less than 600 nucleotides, more preferred less than 500 nucleotides, more preferred less than 400 nucleotides, more preferred less than 300 nucleotides.

In another embodiment, the kit comprises primers of which a 5' primer comprises the nucleotide sequence of SEQ ID NO 1; and a 3' primer comprises the nucleotide sequence of SEQ ID NO 3.

In yet another embodiment, the kit comprises primers of which a 5' primer comprises the nucleotide sequence of SEQ ID NO 2; and a 3' primer comprises the nucleotide sequence of SEQ ID NO 4 or SEQ ID NO 5.

In a further embodiment, the kit comprises primers of which a 5' primer comprises the nucleotide sequence of SEQ ID NO 6; and a 3' primer comprises the nucleotide sequence of SEQ ID NO 3, SEQ ID NO 4 or SEQ ID NO 5.

In another aspect, the invention relates to the use of a method for determining a DRB haplotype in a sample for a genetic application.

The genes of the MHC are known the be among the most polymorphic loci known in human or non-human primates, due to a high rate of mutation and recombination. Major differences between species reside not only in the number and identity of MHC genes, but also in the degree of allelic polymorphism for individual genes. Therefore, the method for determining a DRB-haplotype in a sample, as provided by the current invention, can be used in genetic tests. Genetic test comprise tests to look for a possible predisposition to disease before any symptoms appear.

The most widespread type of genetic testing is newborn screening. Genetic test can be helpful in several areas: early detection, diagnosis, prognosis, and treatment.

In a further embodiment, the method for determining a DRB-haplotype in a sample according to the present invention can be used a genetic application comprising paternity testing.

Paternity tests can be performed postnatally by, for example, testing of blood or testing of a buccal swab, or testing of the umbilical cord, or testing of other sample collection including but not limited to, semen, tissue and hair. Paternity tests can also be performed pre-natally by testing of a sample obtained by amniocentesis or by chorionic villus sampling.

In yet a further embodiment, the method for determining a DRB-haplotype in a sample according to the present invention can be used in a genetic application comprising forensic testing.

Forensic testing includes the application of method for comparison of biological samples in criminal investigations. Typically, the samples are processed in a dedicated forensic laboratory. Short tandem repeats such as provided by the microsatellite in the intron 2 of a DRB-gene may be included in a standard battery of core loci. This may increase the discriminatory power and decrease the probability of a match between profiles of two unrelated persons.

In another embodiment, the method for determining a DRB-haplotype in a sample according to the present invention can be used in a genetic application comprising tissue typing for transplantation testing.

MHC molecules play a crucial role in T-cell activation by antigen presenting cells. Antigenic recognition depends on the interaction between the antigenic peptide-binding MHC molecule and the T-Cell Receptor (TCR), an immunoglobulin-like heterodimeric protein expressed on T-lymphocytes. The transplanted organ represents a continuous source of antigens that can induce a rejection response at any time post-transplant. Furthermore, donor-derived immuno-competent lymphocytes may react with MHC-incompatible recipient cells and induce inflammatory responses in host tissues such as the skin and gastrointestinal tract. This complication is frequent after bone marrow transplantation, but may also affect recipients of liver and other organ transplants and even blood transfusions.

Therefore, transplants with well-matched antigens, especially matching of DRB-haplotype, may function significantly better than those with a poor match, due to different rates of initial immune reactions, graft rejection, and graft failure due to infection or other causes.

In yet another embodiment, the method for determining a DRB-haplotype in a sample according to the present invention can be used in a genetic application comprising testing for chronic or infectious diseases.

Determining a DRB-haplotype may help to determine a possible predisposition to a disease before any symptoms appear. These diseases include, but are not limited to, autoimmune disorders such as arthritis, diabetes, multiple sclerosis (Gregersen et al., 2006. Nature 443: 574-7), bowel diseases such as ulcerative colitis and Crohn's disease, psoriasis, and chronic fatigue syndrome. Furthermore, polymorphisms in MHC class II genes such as DRB genes, have been associated with susceptibility to a range of infectious diseases including malaria, tuberculosis, leprosy, typhoid fever, hepatitis and HIV/AIDS.

In yet another aspect, the invention relates to the use of a kit for determining a DRB haplotype in a cell, said kit comprising means for amplifying at least an intron 2 microsatellite-containing part of at least one DRB-gene, in a genetic application comprising paternity testing, forensic testing, tissue typing for transplantation testing, or testing for chronic or infectious diseases.

Figure 3A:
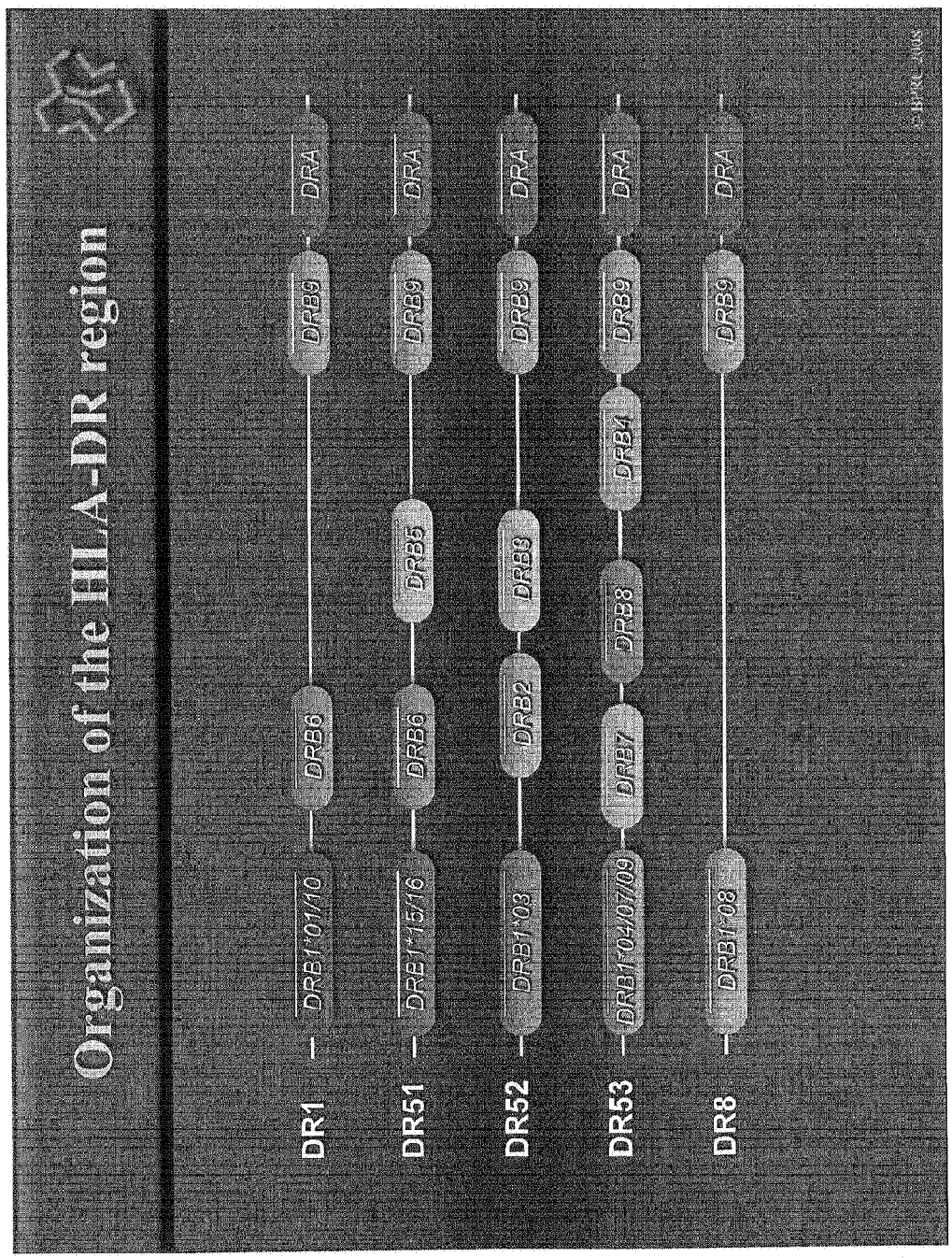
FIG. 3A: Organization of the human (HLA) DR region.
Figure 3B:
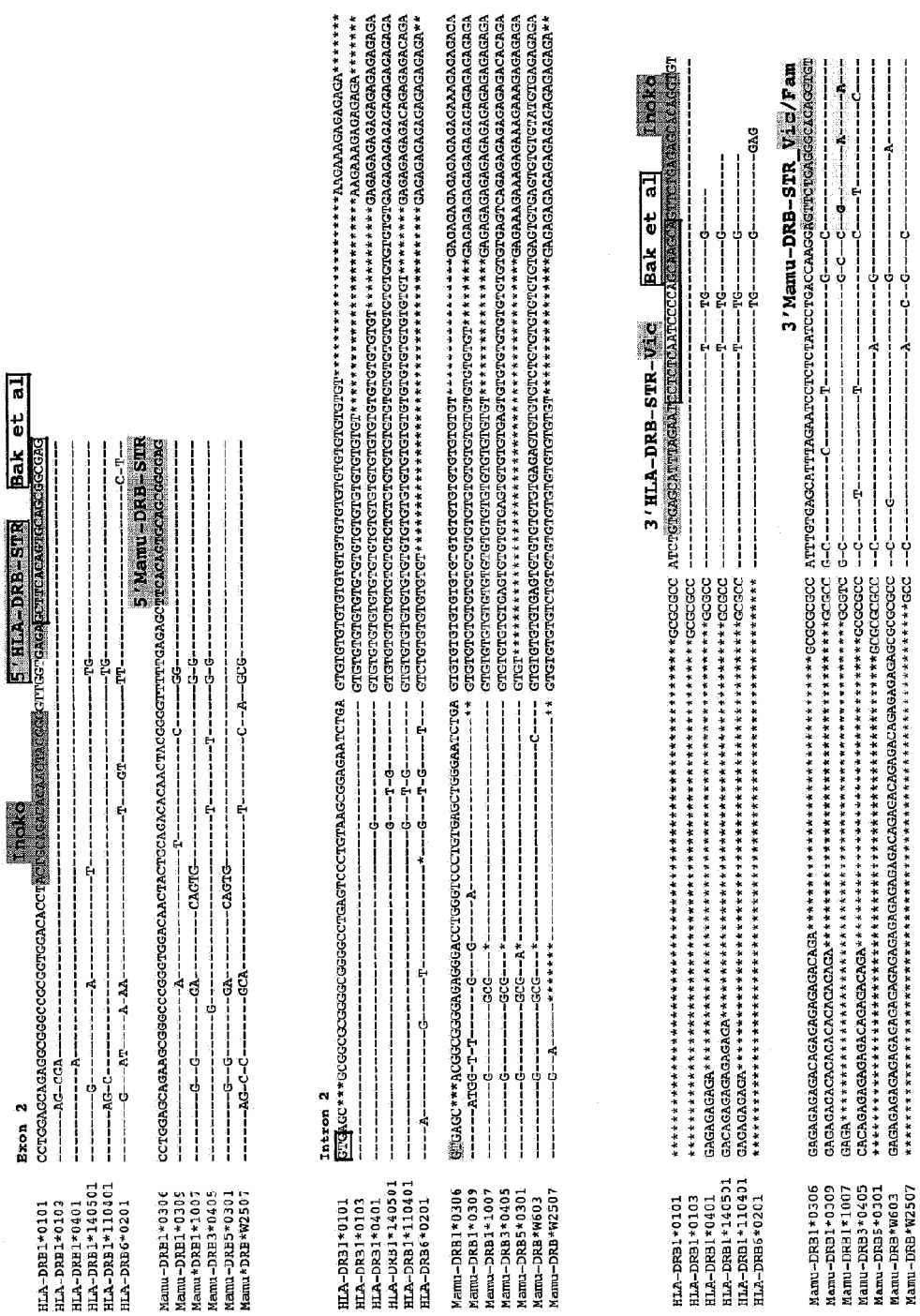
FIG. 3B: Partial nucleotide alignment of DRB exon 2 to intron 2. Primer sequences of different publications are indicated (Doxiadis et al., PNAS 2007, 104, 8907-8912).
Figure 4:
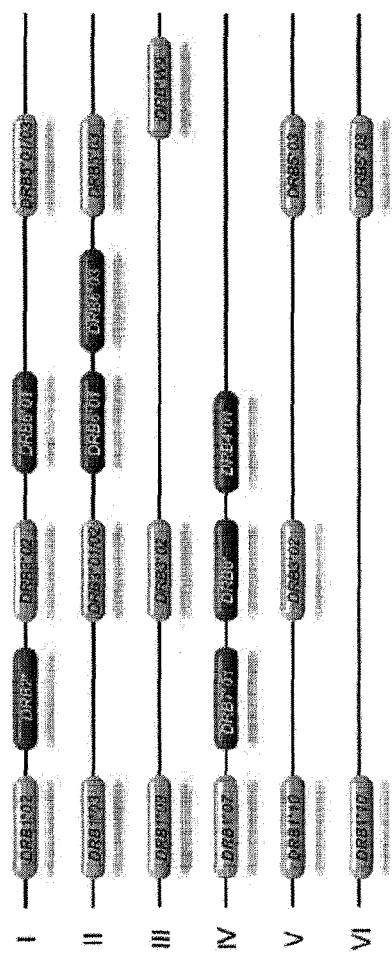
FIG. 4: Organization of the DRB region of the chimpanzee (Patr-DRB).
Figure 5:
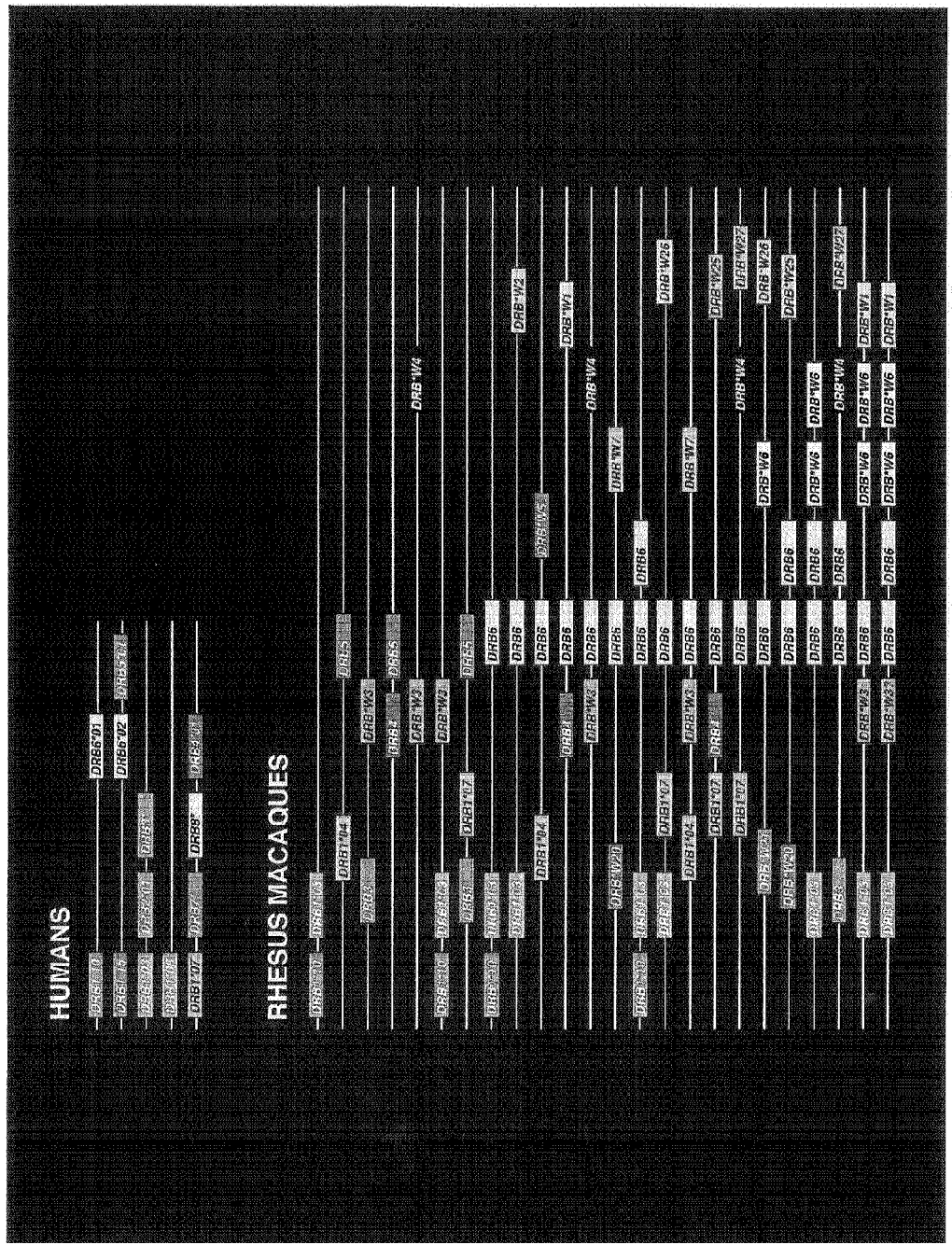
FIG. 5: Organization of the DRB region of humans and rhesus macaques: a comparison.

The DR region of humans (HLA-DR) as well as other primates as chimpanzees and macaques and other mammals as sheep consist of one DRA and one to several DRB loci on each chromosome (here called 'DRB region configurations'). These DRB region configurations vary in number and content of DRB loci present. Examples are given for humans (FIG. 3), chimpanzees (FIG. 4), and rhesus macaques in comparison to humans (FIG. 5). Certain DRB loci are highly polymorphic. Thus, DRB region configurations may display allelic polymorphism and are then called 'DRB haplotypes'. In humans only 5 DRB region configurations are known that are highly polymorphic especially at the DRB1 locus, whereas in rhesus macaques more than 30 region configurations are described which display a low degree of polymorphism (FIG. 5).

Figure 6:
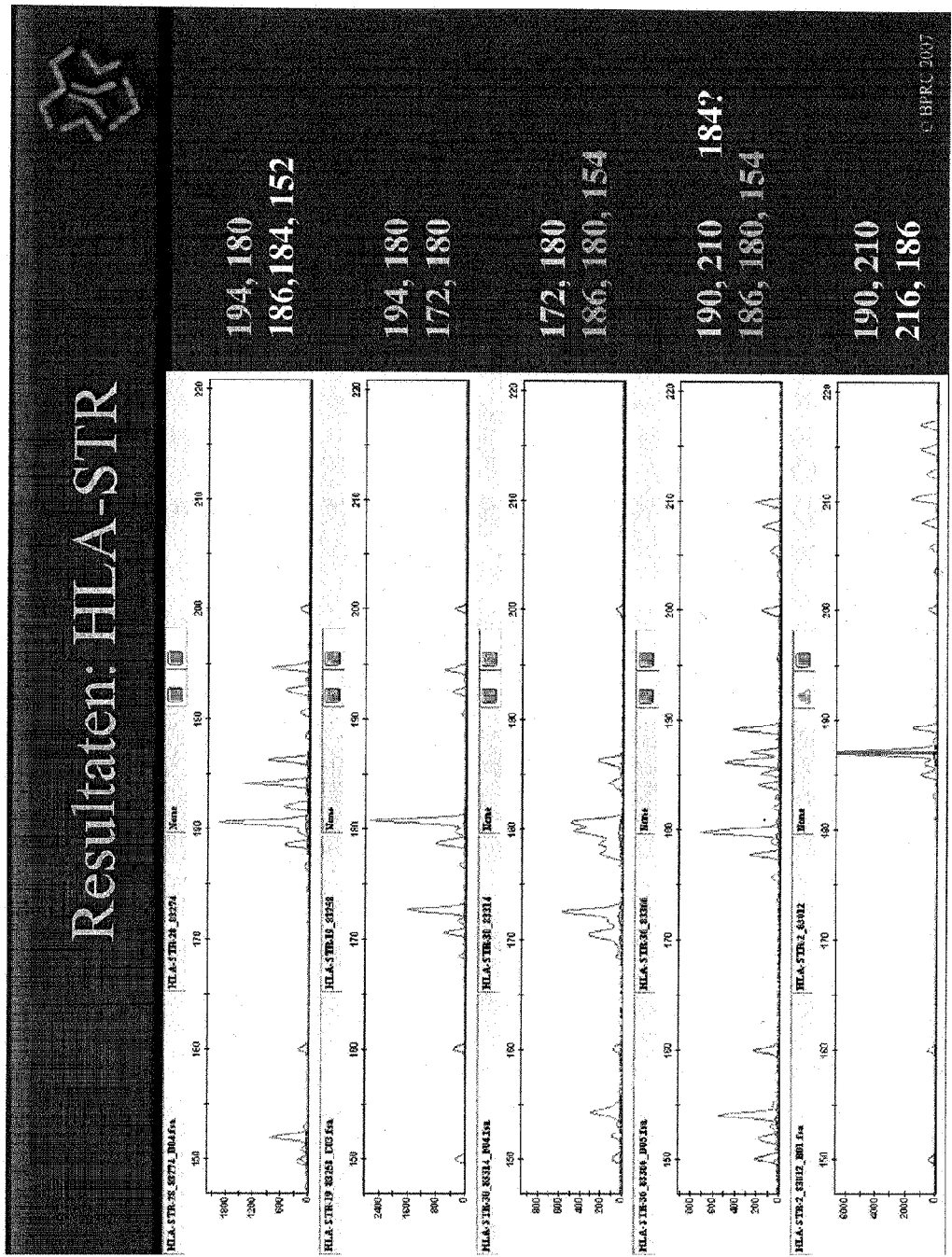
FIG. 6: Results: HLA-STR Example of genotyping of human DRB alleles (HLA) by DRB-STR microsatellite analysis.
Figure 7:
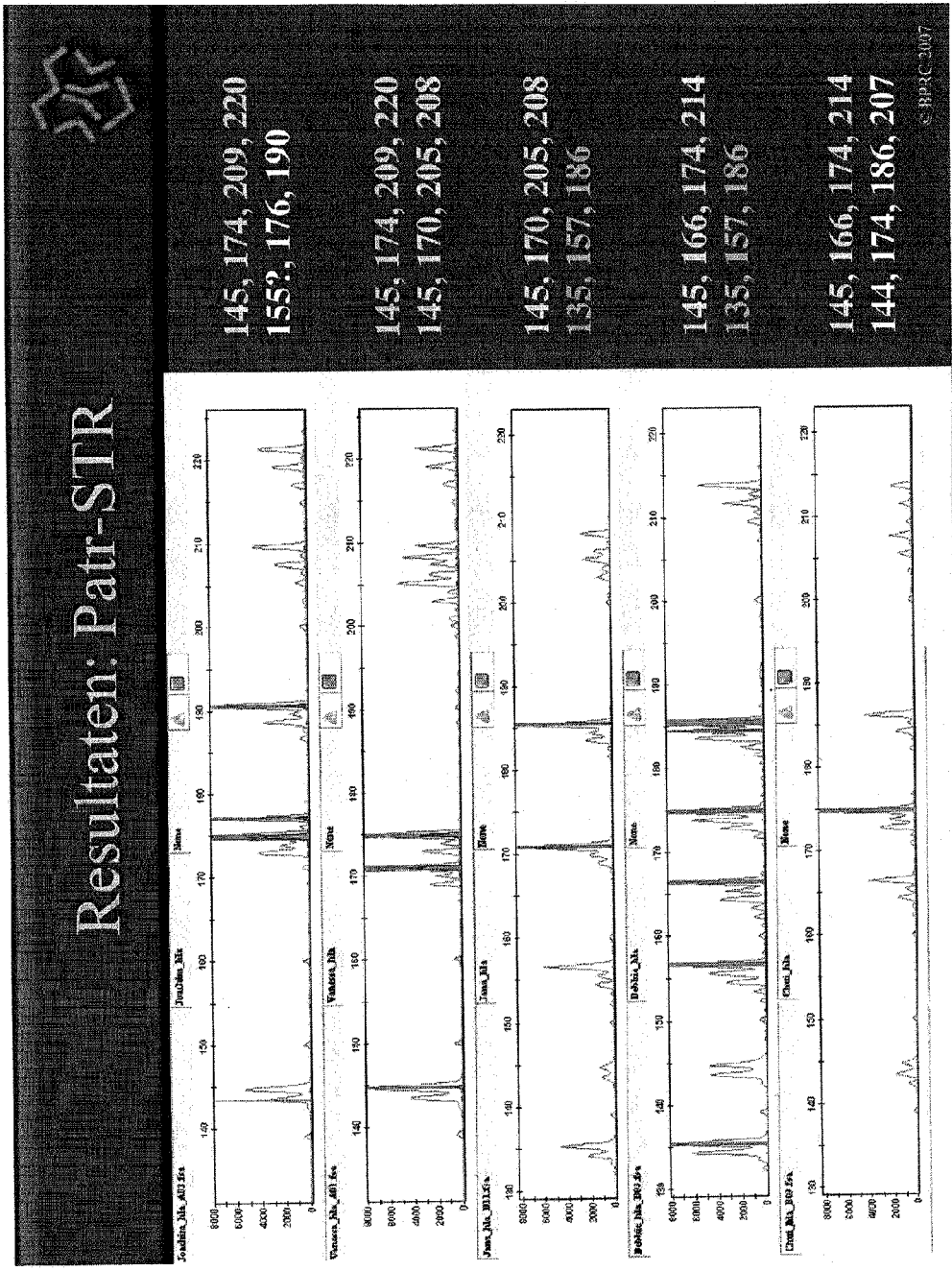
FIG. 7: Example of genotyping of DRB alleles of the chimpanzee (Patr) by DRB-STR microsatellite analysis.
Figure 8:
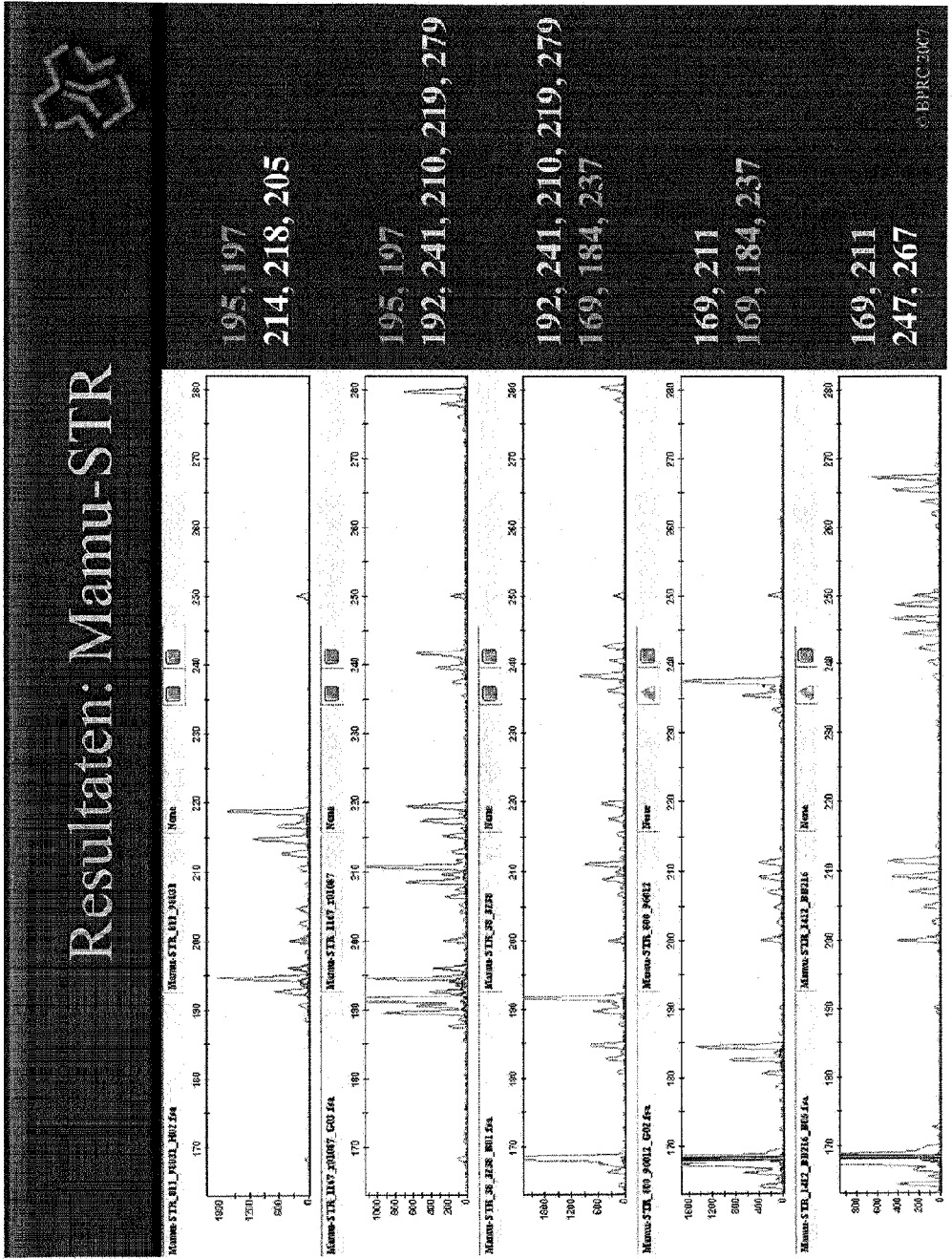
FIG. 8: Example of genotyping of DRB alleles of the rhesus macaque (Mamu) by DRB-STR microsatellite analysis.
Figure 9:
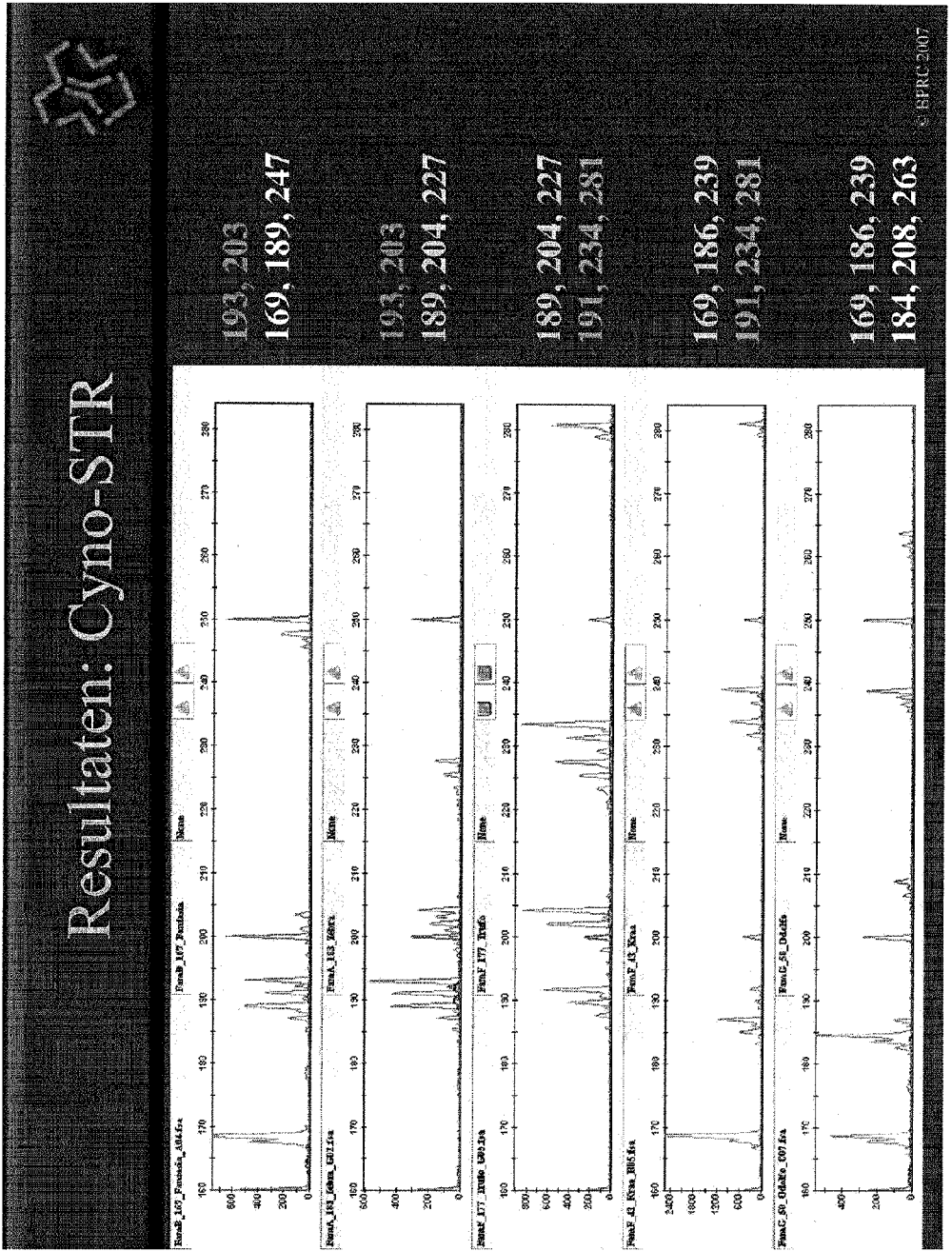
FIG. 9: Example of genotyping of DRB alleles of the cynomolgus macaque (Mafa) by DRB-STR microsatellite analysis.

The present invention describes the possibility to amplify the STR present in intron 2 of all DRB loci, not only DRB1, that contain an exon 2/intron 2 sequence thus all except DRB2 and DRB8. The result of this high-throughput, high-resolution microsatellite typing is a DRB-STR pattern that specifies a given DRB haplotype. Examples for such a DRB-STR length analysis are given for humans (FIG. 6), chimpanzees (FIG. 7), rhesus macaques (FIG. 8) and cynomolgus macaques (FIG. 9). The resulting DRB haplotypes are color-coded. Extensive DRB-STR length analyses of Mhc homozygous individuals or of pedigreed animals of more than 3 generations resulted in the definition of DRB haplotypes of humans and rhesus macaques. Additionally, definition of DRB haplotypes was feasable for chimpanzees (Patr-DRB, Table 4) and cynomalogus macaques (Mafa-DRB, Table 5). Comparison of FIG. 7 and Table 4 shows that the present application allows a definition of 13 instead of six DRB region configurations in the chimpanzee.

Figure 10:
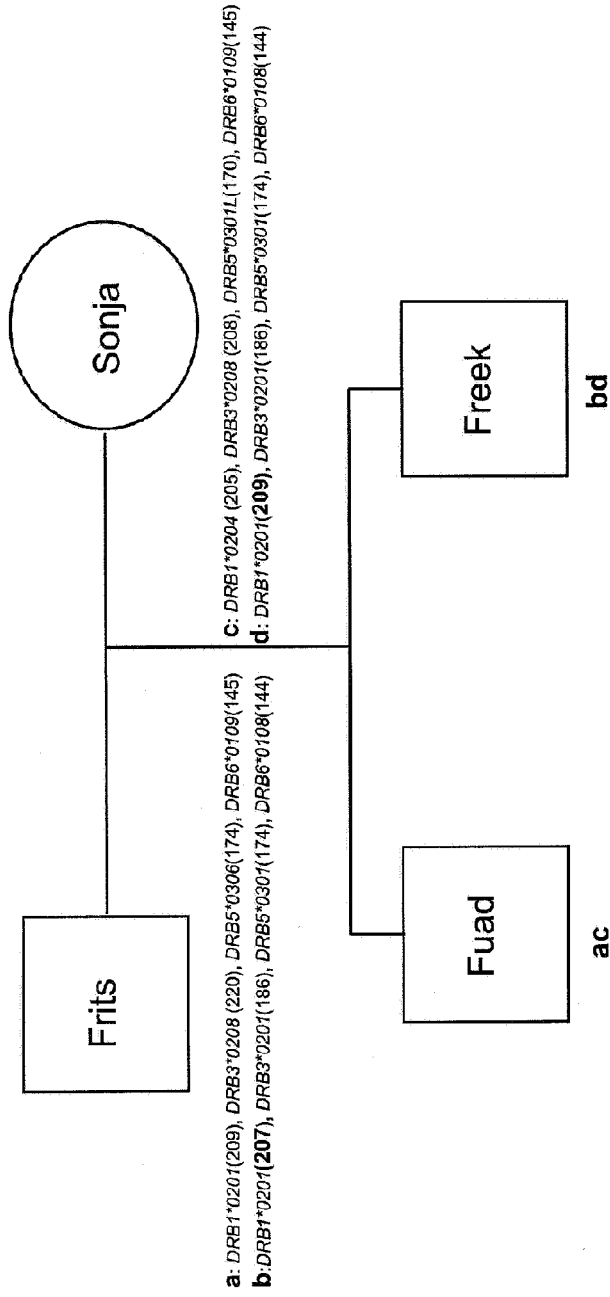
FIG. 10: Example of a paternal and maternal haplotype discrimination by DRB-STR analysis in the chimpanzee (Patr).
Figure 11:
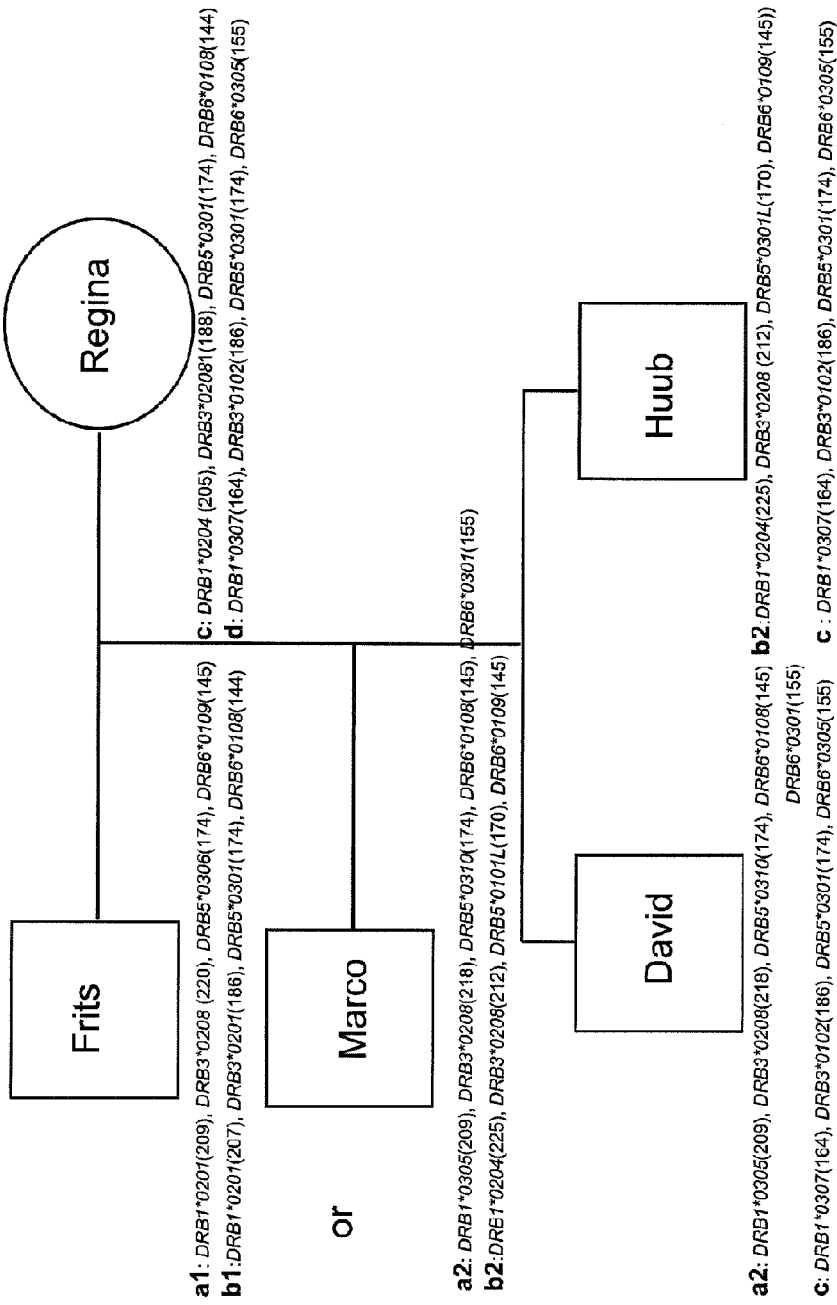
FIG. 11: The use of DRB-STR typing for paternity testing: Example of 2 possible chimpanzee fathers.
Figure 12:
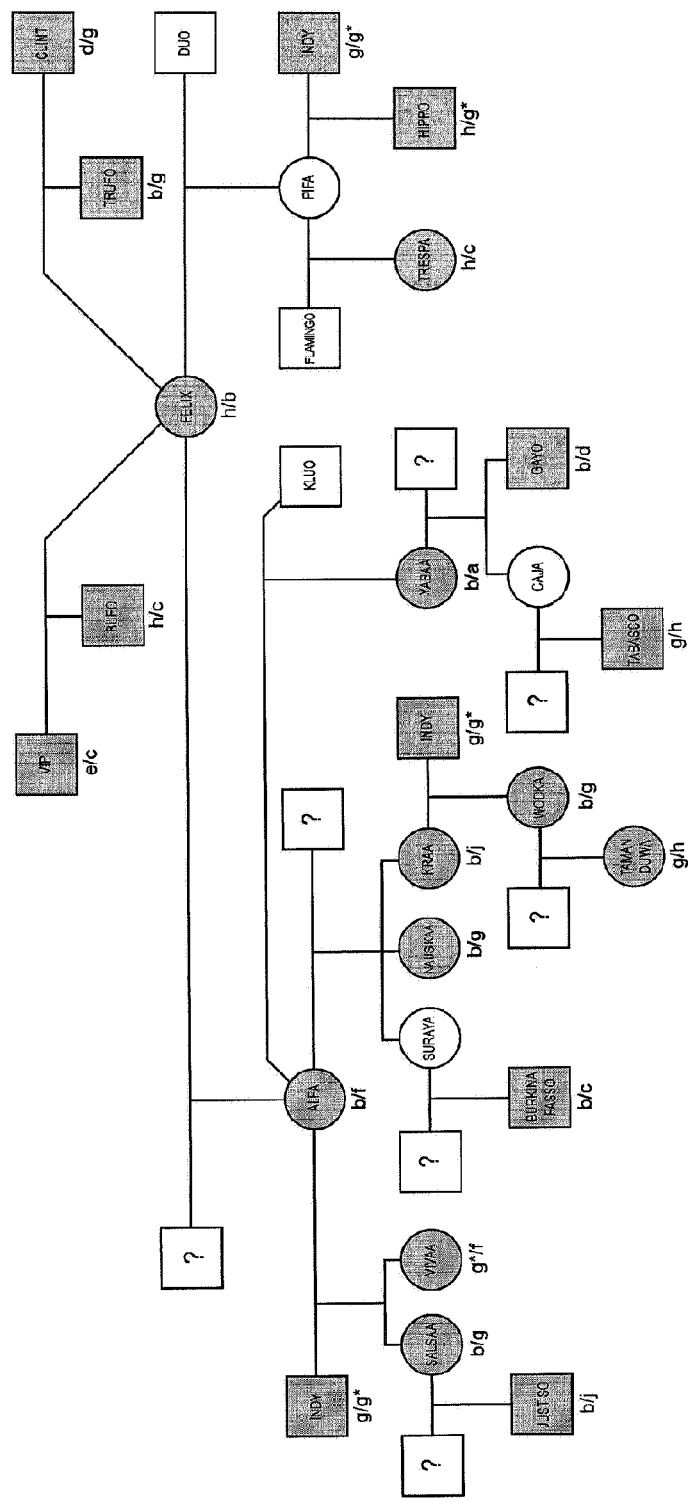
FIG. 12: Pedigree of a cynomolgus macaque family.

The present invention describes the possibility of high resolution typing via DRB haplotyping, not DR/DQ haplotype association studies as claimed by U.S. Pat. No. 5,908, 749 and US 2003/108940 A1. The present invention allows DRB typing in even a higher resolution than exon 2 sequencing, the method-of-choice used for high-resolution typing (van Dijk et al. 2007). An example is given in FIG. 10 for a pedigreed chimpanzee family in which the differentiation between haplotype b of father (Frits) and haplotype d of mother (Sonja) was only possible by DRB-STR typing. Thus, DRB-STR typing as described in the present invention is a powerful method for paternity testing (examples given in FIGS. 10 and 11). Additionally, the present invention allows powerful and quick parentage analysis as needed for example in macaque colony management (FIG. 12).

Furthermore, DRB high resolution typing is useful for disease association studies. In humans it is known that genes of the Major Histocompatibility Complex (Mhc) encode proteins important for activating antigen-specific immune responses. Alleles of the human Mhc class I as well as class II genes are known to be associated with susceptibility as well as resistance to certain autoimmune diseases. Alleles of the HLA-DRB loci are described to be tightly linked with various immune-related diseases as sarcoidosis (Grosser et al. 2005) and chronic pancreatitis (Cavestro et al. 2003). Especially for autoimmune diseases as Addisons' disease, systemic lupus erythematosus (SLE), rheumatoid arthritis (RA), narcolepsia, multiple sclerosis (MS), and type 1 diabetes (T1D) (Carrington 1999; Shiina et al. 2004)(summarized in Shiina, T A, 2006 and reviewed by Carrington 1999) specific DRB alleles or DR/DQ allele combinations are known to be associated with disease susceptibility and/or protection. In RA and Addisons' disease, specific DRB1*04 alleles have been reported to be linked to disease susceptibility (Fries et al. 2002; Gombos et al. 2007). Thus, a high resolution typing for DRB is necessary for the screening of patients for both disorders. Numerous studies have shown a high linkage disequilibrium with HLA-DRB1*1501 with susceptibility to SLE (Graham et al. 2007), Graves' disease (Sasaki et al. 2007), narcolepsy (Planelles et al. 1997) as well as to multiple sclerosis (MS). In narcolepsy and MS disease susceptibility has been fine mapped to the HLA class II haplotype including the HLA-DRB5*0101 allele (Dyment et al. 2004; Dyment et al. 2005; Fogdell et al. 1995; Ramagopalan et al. 2007). The DRB-STR typing method presented here allows high resolution typing and therefore can discriminate between the susceptible alleles DRB1*1501 and DRB5*0101 and their variants DRB1*1502 and DRB5*0201, respectively. This discrimination is otherwise only possible by time-consuming and expensive sequencing techniques. Furthermore, both DRB alleles are shown to encode DR beta chains, which form two different HLA-DR dimers that are both, expressed at significant levels on the cell surface (Prat et al. 2005). Additionally, recent publications showed that epistatic interactions of the two DR molecules have a major influence on the disease development in MS patients (Gregersen et al. 2006). Thus, typing only for the DRB1 allele that is mostly performed by DRB typing procedures may not be sufficient for MS research in the future. On contrast, several chromosomal regions have been linked to T1D susceptibility in humans using modern genome screening methods. The largest contribution comes, however, from several genes in the Mhc complex, formerly known as DR3/DR4. There is evidence that certain residues important for structure and function of both HLA-DQ and -DR peptide binding pockets determine disease susceptibility and resistance (Pociot and McDermott 2002; Zavattari et al. 2001). A number of susceptible, neutral, and protective DR-DQ haplotypes have been identified recently by the T1D Genetics Consortium (Erlich et al. 2008). The most susceptible haplotypes involve DRB1*030/and DRB1*0405/0401/0402, whereas the most protective ones are DRB1*1501 and DRB1*1401. However, allelic variation of DRB can be observed for disease association in different ethnic populations (Al-Harbi et al. 2004; Almawi et al. 2004). Thus, for screening of T1D patients as well as for further fine mapping analysis of other, probably disease associated, loci as DRB5, a quick typing method as described here will be needed.

DEFINITIONS

The term DRB-gene is defined as a functional unit whose inheritance can be followed experimentally. The term DRB gene comprises both an active gene and a pseudogene, the latter being defined as a sequence that closely resembles a known DRB-gene but which is not expressed.

The term DRB-allele is defined as an alternative form of a DRB-gene that can be distinguished from other forms of said DRB-gene by, for example, sequence analyses.

The term DRB-locus is defined as a position on a chromosome that corresponds to a DRB-gene.

The term DRB-haplotype is defined as the unique combination of one or more DRB genes or their evolutionary equivalents that are in most mammals associated in a cis-configuration to the MHC-DRA gene or its evolutionary equivalent on the same chromosome. A DRB-haplotype is determined by the number of DRB-genes, and the specific DRB-alleles that are present of each of the DRB-genes, within the DRB region.

EXAMPLE 1

Materials and Methods

Samples

The 167 rhesus monkeys analyzed, housed at BPRC's breeding colony, originated mostly from India, but some are also of Burmese or Chinese origin. Seven of these animals are completely homozygous for their MHC region and derived from consanguineous matings; two additional animals are homozygous for their Mamu-A, -B, and -DR serotypes. Genomic DNA of human individuals or rhesus macaques was extracted from EDTA blood samples or from immortalized B-cell lines using a standard salting out procedure. Of the 160 human samples tested, 64 were HLA-DRB homozygous, 17 of which belong to a thoroughly characterized homozygous typing cell panel of the XIV International Histocompatibility Workshop, 2005.

STR-DRB genotyping

The relevant DNA segment in rhesus macaques was amplified with a forward primer located at the end of exon 2 (5' Mamu-DRB-STR: TTC ACA GTG CAG CGG CGA GGT) (SEQ ID NO: 2) and 2 labeled reverse primers in intron 2(3' Mamu-DRB-STR_VIC: ACA CCT GTG CCC TCA GAA CT (SEQ ID NO: 4) and 3' Mamu-DRB-STR_FAM_1007: ACA TCT GTG TCC TCA GAC CT (SEQ ID NO: 5)). For human samples a labeled forward primer located at the end of exon 2 (5' HLA-DRB-STR_VIC: GAG AGC TTC ACA GTG CAG C) (SEQ ID NO: 1) and one reverse primer in intron 2 (3' HLA-DRB-STR: GAG AGG ATT CTA AAT GCT CAC) (SEQ ID NO: 3) were used. The labeled primers were synthesized by Applied Biosystems (Foster City, USA) and the unlabeled primers by Invitrogen (Paisley, Scotland). The PCR reaction for rhesus macaques was performed in a 25 ml reaction volume containing 1 unit of Taq polymerase (Invitrogen, Paisley, Scotland) with 0.6 mM of the unlabeled forward primer, 0.4 mM of the VIC labeled reverse primer, 0.2 mM of the FAM labeled reverse primer, 2.5 mM MgCl$_2$, 0,2 mM of each dNTP, 1×PCR buffer II (Invitrogen, Paisley, Scotland) and 100 ng DNA. The PCR mixture for the human STR amplification was the same as that used for rhesus macaques with 0.1 mM of the VIC labeled forward primer and 0.1 mM of the unlabeled reverse primer. The cycling parameters for both amplifications were a 5 min 94° C. initial denaturation step, followed by 5 cycles of 1 min at 94° C., 45 s at 58° C., and 45 s at 72° C. Then the program was followed by 25 cycles of 45 s at 94° C., 30 s at 58° C. and 45 s at 72° C. A final extension step was performed at 72° C. for 30 mM The amplified DNA was prepared for genotyping according to the manufacturer's guidelines and analyzed on an ABI 3130 genetic analyzer (Applied Biosystems). STR, analysis was performed with the Genemapper program (Applied Biosystems) and all samples were analyzed at least twice.

PCR, cloning and sequencing

Seventy-five different Mamu-DRB alleles and 38 HLA-DRB alleles were sequenced from exon 2 to intron 2 including the microsatellite with a generic 5' DRB-exon 2 primer CGT GTC CCC ACA GCA CGT TTC (SEQ ID NO: 6) together with the same 3' primers as used for DRB-STR genotyping but without label. The PCR reactions for rhesus monkey and human DRB were performed in a 100 ml volume containing 4 units of Taq polymerase (Invitrogen, Paisley, Scotland) with 0.2 mM of each primer, 2.5 mM MgCl$_2$, 0,2 mM of each dNTP, 1×PCR buffer II (Invitrogen, Paisley, Scotland) and 200 ng DNA. The cycling parameters were the same as described for STR-DRB genotyping. The resulting amplicons were cloned and sequenced as described recently (Doxiadis et al. 2006. Immunogenetics 58: 259-268; Penedo et al. 2005. Immunogenetics 57, 198-209). The resulting sequences were analyzed using the Sequence Navigator program (Applied Biosystems).

Phylogenetic Analyses

Multiple sequence alignments of exon 2 of human and rhesus macaque -DRB sequences were created using MacVector™ version 8.1.1 (Oxford Molecular Group) and phylogenetic analyses was then performed using PAUP version 4.0b.10 (Swafford 2002. PAUP*. Phylogenetic Analysis Using Parsimony (*and Other Methods). Version 4 (Sinauer Associates, Sunderland, Mass.)). Pairwise distances were calculated using Kimura-2 parameter and the neighbor-joining method for creating a phylogram. Confidence estimates of grouping were calculated according to the bootstrap method generated from 1,000 replicates.

Results

Mamu-DRB Region Configuration Definition by Microsatellite Markers

The rhesus macaques studied are part of a large self-sustaining colony that has been thoroughly pedigreed based on segregation of serologically and molecularly defined markers (Doxiadis et al. 2001. Immunol Rev 183: 76-85; de Groot et al. 2004. J Immunol 172: 6152-7). The current panel covers 22 different region configurations characterized by unique combinations from two to six distinct Mamu-DRB genes (Table 1). Limited allelic polymorphism is detected within region configurations # 1, 11, 15, 18, 19, and 21. To denote allelic variation observed, for instance, in region configuration #1, the relevant haplotypes have been designated 1a and 1b (Table 1). The gene frequencies of the different region configurations as encountered in our population of animals are provided as well, in concert with the number of animals tested. Some haplotypes are frequently observed whereas others appear to be rare (Table 3).

Nearly all Mamu-DRB loci/lineages possess the D6S2878 microsatellite, and the relevant DNA segment could be amplified by means of the unique primer set developed for this protocol (Table 1). Amplification failures have only been observed for a few DRB6/DRBW pseudogenes for which the corresponding amplicons could be scarcely detected, most probably due to primer inconsistencies. The overall results illustrate, however, that the lengths of the amplified STR products are highly variable and range from 153 to 293 by (Table 1). Additionally, various STR markers seem to be predictive for the presence of a particular Mamu-DRB allele and, moreover, family studies demonstrated that they segregate in a Mendelian manner. Subsequent sequencing of the DNA segment ranging from exon 2 to intron 2 was conducted to unequivocally link each D652878 allele to an individual DRB gene/allele. This approach proved that diverse STR lengths could distinguish even highly similar alleles, differing for only one or two nucleotides. An instance is provided by the Mamu-DRB1*07032 and 07033 alleles, which are part of the two haplotypes belonging to configuration #18 (Table 1).

On average, most of the STRs linked to an individual allele appear to be rather conservative in composition and length. In the case of the frequently observed haplotype 11a (Table 3), for example, no length variability for both DRB1 gene-associated D6S2878 alleles is observed, which also holds true for the STR that is linked to DRB5*0301 as seen in haplotype 1a (Table 1). The DRB1*0406-linked STR of the latter configuration, however, may slightly vary in length. Such differences, as can be seen for example in haplotype 12, are reproducible, and do segregate in families with a particular haplotype as defined by serological methods (Bontrop et al. 1995. Immunol Rev 143: 33-62). As each region configuration is composed of an exclusive combination of different Mamu-DRB genes, the most essential conclusion that can be drawn is that the combination of STR markers appears to be unique for a given region configuration/haplotype.

HLA-DRB Haplotype Definition by Microsatellite Analysis

Genotyping for the highly divergent (GT)x(GA)y microsatellite allows speedy and accurate DR haplotyping in rhesus macaques, a species known to possess a high number of region configurations; these display, however, low levels of allelic variation. Next, it was investigated whether the same approach would work in a species, that possesses a relatively low number of region configurations that parade abundant levels of allelic polymorphism. Therefore, in the first instance, a thoroughly characterized panel of 160 unrelated human samples of Caucasoid origin was chosen to conduct such an analysis. This selection also comprised 64 homozygous typing cells, facilitating the simple definition of haplotypes. Furthermore, the panel included the five known HLA-DRB region configurations, designated DR8, DR1, DR51, DR52, and DR53 (Schreuder et al. 2005. Tissue Antigens 65: 1-55), but also covered the 13 most common DR serotypes present in the Caucasoid population, differing for their DRB1 alleles (Table 2). To denote allelic variation as observed within some serotypes, the different DRB haplotypes have been designated a, b, c and so on (Table 2). The number of samples tested per haplotype, as well as the gene frequencies of the serotypes (Marsh et al. 2000. The HLA FactsBook (Academic Press, London, UK, San Diego)), have also been summarized (Table 3).

Again, a specially designed generic primer pair allowed amplification of the relevant intron 2 segment for virtually all HLA-DRB genes/alleles. Amplification failed only for one particular HLA-DRB5 allele present on DR16 haplotypes. This may be due to a mutated primer site. Subsequent extensive sequencing of exon 2-intron 2 DNA segments verified for each of the HLA-DRB alleles the unique linkage to its adjacent D6S2878 allele. The lengths of the respective repeats are highly polymorphic in the human population as well and range from 135 to 220 by (Table 2). Moreover, STR lengths are highly predictive for the presence of individual HLA-DRB alleles, as was also shown earlier for rhesus monkeys. Again, differential STR lengths can make the distinction between highly similar -DRB alleles, differing for a few nucleotides: for example in the case of DRB1*0801 (03) and DRB1*080302 (Table 2). The DR53 region configuration contains a pseudogene, named HLA-DRB7, which is absent in macaques. This pseudogene displays no allelic variation, and indeed the associated D6S2878 is invariant in length independent of the adjacent -DRB1 allele. Thus, the DRB7-associated STR typifies all the haplotypes belonging to the DR53 region configuration (Table 2). The same holds true for the DRB6 allele and its adjacent STR, which are characteristic for the DR1 region configuration, covering the DR1 and DR10 serotypes. As observed in rhesus macaques, some HLA-DRB alleles appear to be associated with multiple D6S2878 variants. A case is provided by the HLA-DRB1*140101 allele observed within the DR14 haplotypes, but some of the repeats grouping in the DR11a and DR13c family of haplotypes also show length differences (Table 2). Family analyses are needed to demonstrate their segregation. Most of the human repeats, however, appear to be conservative in composition and length, and are linked to an individual allele. Within this panel of 30 different HLA-DRB haplotypes, all but two can be readily dissected based on by their D6S2878 profiles. Thus, complex DR region configuration/haplotype information, as present in at least two populations of primate species, is readily obtained and defined based on D6S2878 genotyping after a simple amplification protocol conducted with one primer set.

Figure 1:
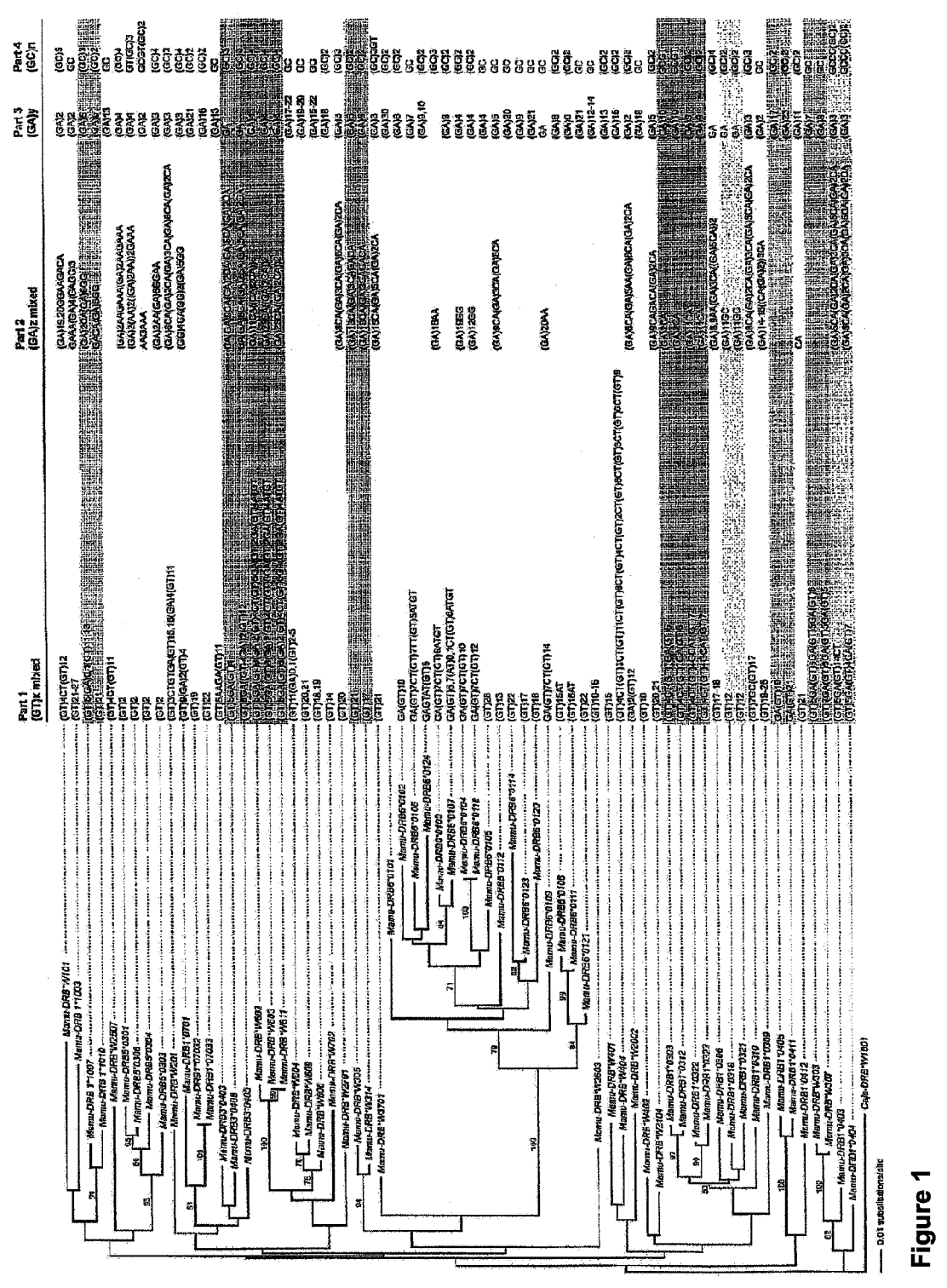

Genetic stability and evolutionary history of the STR-DRB complex The D6S2878 microsatellite has a composite character in primates (Riess et al. 1990. Immunogenetics 32: 110-6; Bergstrom et al. 1999. Am J Hum Genet 64: 1709-18; Kriener et al. 2000. Immunogenetics 51: 169-78; Trtkova et al. 1995. Mol Phylogenet Evol 4: 408-19) and phylogenetic comparisons of different DRB1 sequences obtained from humans and chimpanzees indicated that the ancestral structure most likely must have been a (GT)x(GA)y dinucleotide repeat. The HLA-DRB1 associated microsatellite comprises three sections exhibiting different evolutionary stabilities. The 5'(GT)x repeat represents the longest segment and evolves most rapidly, which is a known feature for long, uninterrupted dinucleotide repeats. The middle section or the (GA)z part is shorter and interrupted; its constellation appears to correlate well with different lineages/loci and its length seems to segregate with specific DRB1 alleles. The length of the 3'(GA)y part appears to be specific for a certain DRB lineage/locus (Bergstrom et al. 1999. Am J Hum Genet 64: 1709-18). All HLA-DRB exon 2 sequences described in this study have been subjected to phylogenetic analyses, on which the D6S2878 sequences have been superimposed (FIG. 1). As can be seen, this report extends the knowledge on this particular microsatellite but also underscores its compound character (Epplen et al. 1997. Hum Genet 99: 399-406; Bergstrom et al. 1'999. Am J Hum Genet 64: 1709-18). Additionally, a short dinucleotide (GC)1-3 part could be observed at the 3' end of the microsatellite of all HLA-DRB genes except for those belonging to the DRB6 and DRB7 pseudogenes. The variation seen in this newly recognized section of the microsatellite seems to be prognostic for certain HLA-DRB lineages or loci, respectively. The 5'(GT)x part is indeed the most polymorphic, which may especially in the case of fairly long (GT)x repeats evolve faster than the mutation rate operative on exon 2 itself (FIG. 1). This phenomenon, already described for DQCAR (Lin et al. 1998. Tissue Antigens 52: 9-18) could explain why, for instance, the HLA-DRB1*1302 allele is associated with a STR displaying length variation (Table 2).

The ancient HLA-DRB6 and -7 pseudogenes appear to miss the middle, interrupted (GA)z or the (GA)y part, respectively. The HLA-DRB6*0101 gene harbors a genetically stable D6S2878 showing no length differences at all. This is most probably due to its composition represented by a short and interrupted 5'(GT) and 3'(GA) part (Petes et al. 1997. Genetics 146: 491-8; Wierdl et al. 1997 Genetics 146: 769-79). For HLA-DRB6*0201 the opposite is true, and the long and uninterrupted (GT)x and (GA)y parts are indicative for unstable STR lengths (Table 2 and FIG. 1) (Jin et al. 1996. Proc Natl Acad Sci USA 93: 15285-8).

The Mamu-DRB exon 2 sequences have also been subjected to phylogenetic analyses and the genetic composition of the D6S2878 sequences has been superimposed (FIG. 2). Like in humans, D6S2878 has a compound character. The newly described fourth 3'(GC) dinucleotide part is also present in rhesus macaques with repeat lengths ranging from 1 to 5. Comparable to the human situation, Mamu-DRB6 alleles form a distinct Glade in the phylogenetic tree. Since the DRB6 locus is thought to predate the divergence of Old World monkeys, great apes, and homonoids, it is not surprising that the same ancestral (GT)x(GA)y structure was detected in rhesus monkeys just as in humans. In contrast to the human microsatellite, some Mamu-DRB lineages/loci are characterized by a multipart (GT)x and/or a (GA)z middle segment. In general, the rhesus macaque STR appears to be even more complex than its human equivalent. This multifaceted composition seems to correlate with the high number of DRB region configuration/haplotype diversity observed in rhesus macaques. Despite the complex microsatellite patterns observed in the rhesus macaque, the composition and length of repeats associated with known Mamu-DRB alleles, are as expected, highly similar. The rhesus macaque DRB region has been subject to several rounds of duplication and contraction processes. For that reason, it is difficult to understand which highly related genes located on different region configurations/haplotypes represent separate loci or whether these sequences have an allelic affiliation. This microsatelite will be helpful in sorting out such genetic relationships.

Discussion

Microsatellite D6S2878 is considered to represent a promising marker for the development of a quick and accurate DRB haplotyping protocol in primate species, on the condition that one single set of informative primers can be developed. Indeed, a specifically designed primer pair allowed amplification of the relevant intron 2 segment for virtually all HLA—as well as Mamu-DRB genes/alleles. For both species, amplification artifacts have rarely been observed and such types of problems are easily to overcome by designation of specific primers that can be added to the same reaction mixture. The D6S2878 STR was proven to be highly variable in length, not only in humans but also in the rhesus macaque, thus verifying this microsatellite as a useful marker for DRB typing of both species. Phylogenetic analyses of human as well as rhesus macaque exon 2 sequences have been performed and compared with microsatellite composition. For humans, the evolutionary relationships of exon 2 and the adjacent microsatellite seem to segregate closely together (FIG. 1). In rhesus macaques, the microsatellite composition was far more variable than in humans and a comparison of microsatellite and exon 2 phylogeny does not always seem to match the microsatellite composition (FIG. 2). One explanation for these results may be that rhesus macaque DRB loci/lineages are much older than their human equivalents, and this can be the reason for the higher diversity of the adjacent microsatellite as well. Furthermore, preliminary results of intron sequences illustrate that some of the Mamu-DRB sequences that are considered alleles of a given locus probably represent monomorphic loci themselves. However, truly allelic variants manifest the reliability of the comparison of exon 2 and the D6S2878 marker not only in humans but also in rhesus macaques.

Microsatellite typing was, in the first instance performed on large human and rhesus macaque panels for which the typing information was known. The most essential conclusion to be drawn (Table 1 and 2) is that in both species the combination of STR markers appears to be unique for a given haplotype. Within the rhesus macaque panel of 31 haplotypes all could be defined unambiguously, within the human panel of 30 haplotypes all but two could be thus defined. As stated earlier, ambiguities can easily be solved by development of additional primer pairs. As a control, a blind test was performed with 47 human and 26 rhesus monkey samples. More than 90% of the samples were scored correctly for their Mhc-DRB haplotypes. Some of the samples were not scored properly because they contained allotypes that were not present in the original test panel. Thus, this D6S2878 typing protocol provides a highly reliable method for Mamu- and HLA-DRB haplotyping, with its main advantage being simplicity and speed. Since differently labeled primers can be used for microsatellite typing, multiplexing is possible and 96 samples or even more can be analyzed within one test panel. The simplicity of the test is especially useful for Mamu-DRB haplotyping, which is otherwise extremely time consuming due to the unprecedented high number of different -DRB region configurations. For the human situation, this approach is very helpful in the analysis of large amounts of samples, as they are needed, for example, in population and/or disease association studies. Furthermore, this method may also be of use in forensic medicine as well as in paternity-testing protocols. Additionally, high-resolution -DRB haplotyping will simplify donor-recipient matching in organ as well as bone marrow transplantation. As the D6S2878 STR is an old entity, it may also be used to study other populations of primate species.

The evolutionary stability of this microsatellite has been a matter of debate (Epplen et al. 1997. Hum Genet 99: 399-406; Riess et al. 1990. Immunogenetics 32: 110-6; Bergstrom et al. 1999. Am J Hum Genet 64: 1709-18; Trtkova et al. 1995. Mol Phylogenet Evol 4: 408-19; Maueler et al. 1999. Gene 226: 9-23). The HLA-DRB7 associated D6S2878 allele is especially remarkable, as this repeat has the shortest (GT)x as well as the (GA)y part and is highly stable in length, showing no polymerase slippage at all. This is in accordance with the fact that short and/or interrupted repeats are more stable than long, uninterrupted dinucleotides (Petes et al. 1997. Genetics 146: 491-8; Wierdl et al. 1997. Genetics 146: 769-79; Jin et al. 1996. Proc Natl Acad Sci USA 93: 15285-8). To what extent the repeat composition may have a direct or indirect influence on the low mutation rate of the adjacent exon 2 segment of the DRB7 pseudogene is not well understood at present. It has been proposed, for example, that microsatellites near genes may increase and probably also decrease local mutation rates (Vowles and Amos 2004. PLoS Biol 2: E199). Interestingly, exon 2 of the DRB7 pseudogene, present on the only shared DR region configuration of humans and chimpanzees, is highly conserved between both species. Moreover, the D6S2878 sequence is completely identical (FIG. 1). It has been suggested that the intron 2 segment containing the (GT)x(GA)y repeat may bind a zinc-dependent protein and forms non B-DNA structures; thus, functionality of these so-called 'junk' DNA sequences cannot be ruled out and should be subjected to further analysis (Maueler et al. 1999. Gene 226: 9-23).

Additional References

Al-Harbi, E. M., Abbassi, A. J., Tamim, H., al-Jenaidi, F., Kooheji, M., Kamal, M., al-Mahroos, S., al-Nasir, F., Motala, A. A., and Almawi, W. Y.: Specific HLA-DRB and -DQB alleles and haplotypes confer disease susceptibility or resistance in Bahraini type 1 diabetes patients. *Clin Diagn Lab Immunol* 11: 292-6, 2004

Almawi, W. Y., Abou-Jaoude, M. M., Tamim, H., Al-Harbi, E. M., Finan, R. R., Wakim-Ghorayeb, S. F., and Motala, A. A.: Distribution of HLA class II (DRB1/DQB1) alleles and haplotypes among Bahraini and Lebanese Arabs. *Transplant Proc* 36: 1844-6, 2004

Bak, E. J., Ishii, Y., Omatsu, T., Kyuwa, S., Tetsuya, T., Hayasaka, I., and Yoshikawa, Y.: Identification and analysis of MHC class II DRB1 (Patr-DRB1) alleles in chimpanzees. *Tissue Antigens* 67: 134-42, 2006

Carrington, M. M., D.; Wade, J.; Klitz, W.; Barcellos, 1.; Thomson, G.; Chen, J.; Truedsson, L.; Sturfelt, G.; Alper, D.; Awdeh, Z.; Huttley, G.: Microsatellite markers in complex disease: mapping disease-associated regions within the human major histocompatibility complex. In G. D. B. a. S. C (ed.): *Microsatellites: Evolution and Applications*, pp. 225-237, Oxford University Press, Oxford, 1999

Cavestro, G. M., Frulloni, L., Neri, T. M., Seghini, P., Nouvenne, A., Zanetti, A., Bovo, P., Di Mario, F., Okolicsanyi, L., and Cavallini, G.: Association of HLA-DRB1*0401 allele with chronic pancreatitis. *Pancreas* 26: 388-91, 2003

Dyment, D. A., Ebers, G. C., and Sadovnick, A. D.: Genetics of multiple sclerosis. *Lancet Neurol* 3: 104-10, 2004

Dyment, D. A., Herrera, B. M., Cader, M. Z., Willer, C. J., Lincoln, M. R., Sadovnick, A. D., Risch, N., and Ebers, G. C.; Complex interactions among MHC haplotypes in multiple sclerosis: susceptibility and resistance. *Hum Mol Genet* 14: 2019-26, 2005

Erlich, H., Valdes, A. M., Noble, J., Carlson, J. A., Varney, M., Concannon, P., Mychaleckyj, J. C., Todd, J. A., Bonella, P., Fear, A. L., Lavant, E., Louey, A., and Moonsamy, P.: HLA DR-DQ Haplotypes and Genotypes and Type 1 Diabetes Risk: Analysis of the Type 1 Diabetes Genetics Consortium Families. *Diabetes*, 2008

Fogdell, A., Hillert, J., Sachs, C., and Olerup, O.: The multiple sclerosis- and narcolepsy-associated HLA class II haplotype includes the DRB5*0101 allele. *Tissue Antigens* 46: 333-6, 1995

Fries, J. F., Wolfe, F., Apple, R., Erlich, H., Bugawan, T., Holmes, T., and Bruce, B.: HLA-DRB1 genotype associations in 793 white patients from a rheumatoid arthritis inception cohort: frequency, severity, and treatment bias. *Arthritis Rheum* 46: 2320-9, 2002

Gombos, Z., Hermann, R., Kiviniemi, M., Nejentsev, S., Reimand, K., Fadeyev, V., Peterson, P., Uibo, R., and Ilonen, J.: Analysis of extended human leukocyte antigen haplotype association with Addison's disease in three populations. *Eur J Endocrinol* 157: 757-61, 2007

Graham, R. R., Ortmann, W., Rodine, P., Espe, K., Langefeld, C., Lange, E., Williams, A., Beck, S., Kyogoku, C., Moser, K., Gaffney, P., Gregersen, P. K., Criswell, L. A., Harley, J. B., and Behrens, T. W.: Specific combinations of HLA-DR2 and DR3 class II haplotypes contribute graded risk for disease susceptibility and autoantibodies in human SLE. *Eur J Hum Genet* 15: 823-30, 2007

Gregersen, J. W., Kranc, K. R., Ke, X., Svendsen, P., Madsen, L. S., Thomsen, A. R., Cardon, L. R., Bell, J. I., and Fugger, L.: Functional epistasis on a common MHC haplotype associated with multiple sclerosis. *Nature* 443: 574-7, 2006

Grosser, M., Luther, T., Fuessel, M., Bickhardt, J Magdolen, V., and Baretton, G.: Clinical course of sarcoidosis in dependence on HLA-DRB1 allele frequencies, inflammatory markers, and the presence of *M. tuberculosis* DNA fragments. *Sarcoidosis Vase Diffuse Lung Dis* 22: 66-74, 2005

Planelles, D., Puig, N., Beneto, A., Gomez, E., Rubio, P., Mirabet, V., Bonanad, S., Blasco, I., and Montoro, J. A.: HLA-DQA, -DQB and -DRB allele contribution to narcolepsy susceptibility. *Eur J Immunogenet* 24: 409-21, 1997

Pociot, F. and McDermott, M. F.: Genetics of type 1 diabetes mellitus. *Genes Immun* 3: 235-49, 2002

Prat, E., Tomaru, U., Sabater, L., Park, D. M., Granger, R., Kruse, N., Ohayon, J. M., Bettinotti, M. P., and Martin, R.: HLA-DRB5*0101 and -DRB1*1501 expression in the multiple sclerosis-associated HLA-DR15 haplotype. *J Neuroimmunol* 167: 108-19, 2005

Ramagopalan, S. V., Morris, A. P., Dyment, D. A., Herrera, B. M., DeLuca, G. C., Lincoln, M. R., Orton, S. M., Chao, M. J., Sadovnick, A. D., and Ebers, G. C.: The inheritance of resistance alleles in multiple sclerosis. *PLoS Genet* 3: 1607-13, 2007

Sasaki, M., Yuzawa, M., Saito, T., Ikoma, A., Tamemoto, H., Kawakami, M., and Ishikawa, S. E.: New HLA DRB1 and DQB1 haplotypes in a pedigree of familial Graves' disease in Japan. *Endocr J* 54: 721-5, 2007

Shiina, T., Inoko, H., and Kulski, J. K.: An update of the HLA genomic region, locus information and disease associations: 2004. *Tissue Antigens* 64: 631-49, 2004 van Dijk, A., Melchers, R., Hilkes, Y., Rozemuller, E., and Tilanus, M.: HLA-DRB sequencing-based typing: an improved protocol which shows complete DRB exon 2 sequences and includes exon 3 of HLA-DRB4/5. *Tissue Antigens* 69 Suppl 1: 61-3, 2007

Zavattari, P., Lampis, R., Motzo, C., Loddo, M., Mulargia, A., Whalen, M., Maioli, M., Angius, E., Todd, J. A., and Cucca, F.: Conditional linkage disequilibrium analysis of a complex disease superlocus, IDDM1 in the HLA region, reveals the presence of independent modifying gene effects influencing the type 1 diabetes risk encoded by the major HLA-DQB1, -DRB1 disease loci. *Hum Mol Genet* 10: 881-9, 2001

TABLE 1

Mamu-DRB haplotypes defined by exon 2 sequencing and D6S2878 genotyping

| hapl | 1st DRB locus | STR | 2nd DRB locus | STR | 3rd DRB locus | STR |
|---|---|---|---|---|---|---|
| 1a | DRB1*0406 | 205, 207, 211 | DRB5*0301 | 169 | | |
| 1b | DRB1*0411 | 223 | DRB5*0304 | 153 | | |
| 2 | DRB3*0403 | 192 | DRB*W305 | 227 | | |
| 3[a] | DRB1*0412 | 199 | DRB*W3701 | 235 | | |
| 4[a] | DRB1*1010 | 205 | DRB6*0121 | 216 | | |
| 5[a] | DRB3*0408 | 203 | DRB*W404 | 293 | | |
| 6[a] | DRB3*0411 | 190 | DRB*W314 | 219 | | |
| 7[b] | DRB4*0102 | 291 | DRB5*0306 | 173 | | |
| 8[b] | DRB1*0321 | 181 | DRB1*0322/3 | 209 | | |
| 9[b] | DRB1*0321 | 181 | DRB1*0322/3 | 209 | DRB1*1003[c] | 175? |
| 10[b] | DRB1*0309 | 229 | DRB*W2507 | 181 | DRB6*0109 | ? |

TABLE 1-continued

Mamu-DRB haplotypes defined by exon 2 sequencing and D6S2878 genotyping

| | | | | | | | |
|---|---|---|---|---|---|---|---|
| 11a | DRB1*0303 | 195 | DRB1*1007 | 197 | DRB6*0103 | (202-206) | |
| 11b | DRB1*0312 | 195 | DRB1*1007 | 201 | DRB6*0103 | ? | |
| 11c | DRB1*0306 | 226 | DRB1*1007 | 197 | DRB6*0103 | ? | |
| 11d | DRB1*0306 | 226-230 | DRB1*1003 | 199-213 | DRB6*0107 | 182 | |
| 12 | DRB1*0309 | 233-247 | DRB6*0101 | ? | DRB*W201 | 263 (261, 267) | |
| 13 | DRB6*0112 | 214 | DRB*W2501 | 218? | DRB*W2002 | 218 | |
| 14 | DRB6*0114 | 218 | DRB*W303 | 193 | DRB*W401 | 187 | |
| 15a | DRB1*0403 | 229 | DRB6*0107 | 184 | DRB*W501 | ? | |
| 15b[b] | DRB1*0403 | 229 | DRB6*0107 | 183 | DRB*W502 | ? | |
| 16 | DRB1*0404 | 225 | DRB6*0102 | 164 | DRB*W307 | 195 | |
| 17 | DRB1*0701 | 197 | DRB3*0405 | 237 | DRB5*0303 | 169 | |
| 18a[a] | DRB1*0326 | 214 | DRB1*07032 | 211 | DRB6*0124 | 170 | |
| 18b[b] | DRB1*0326 | 214 | DRB1*07033 | 207 | DRB6*0124 | 168 | |
| 19a | DRB1*0318 | 181 | DRB6*0105 | 190, 192 | DRB*W604 | 201, 205 | |
| 19b | DRB1*0318 | 181 | DRB6*0105 | 194 | DRB*W604 | 197 | |
| 20[a] | DRB3*0403 | 182 | DRB*W402 | 185 | DRB*W2701 | 227 | |
| 21a | DRB6*0111 | 178 | DRB*W606 | 211, 213, 197 | DRB*W2104 | 211, 213 | |
| 21b[b] | DRB6*0108 | 176 | DRB*W606 | 213 | DRB*W2104 | 213 | |
| 22 | DRB1*0310 | 241 | DRB6*0118 | 210 | DRB*W101 | 219, 223 | |

| hapl | 4th DRB locus | STR | 5th DRB locus | STR | 6th DRB locus | STR |
|---|---|---|---|---|---|---|
| 1a | | | | | | |
| 1b | | | | | | |
| 2 | | | | | | |
| 3[a] | | | | | | |
| 4[a] | | | | | | |
| 5[a] | | | | | | |
| 6[a] | | | | | | |
| 7[b] | | | | | | |
| 8[b] | | | | | | |
| 9[b] | | | | | | |
| 10[b] | | | | | | |
| 11a | | | | | | |
| 11b | | | | | | |
| 11c | | | | | | |
| 11d | | | | | | |
| 12 | | | | | | |
| 13 | DRB6*0106? | 205? | | | | |
| 14 | | | | | | |
| 15a | DRB6*? | 208 | | | | |
| 15b[b] | DRB6*0120 | 208 | | | | |
| 16 | DRB*W702 | 188 | | | | |
| 17 | DRB6*0123 | 184 | | | | |
| 18a[a] | DRB*W2603 | 177 | DRB6*0120 | ? | | |
| 18b[b] | DRB*W2604 | 177 | DRB6*0120 | 208 | | |
| 19a | DRB*W603 | 275, 277 | DRB6*0104(+ALU) | 222 (220) | | |
| 19b | DRB*W611 | 275 | DRB6*01? | 222 | | |
| 20[a] | DRB6*0116 | 206 | DRB6*0107 | 182 | | |
| 21a | DRB*W2603 | 177, 187 | DRB6*0122 | 236 | | |
| 21b[b] | DRB*W2604 | 177 | DRB6*0122 | 232 | | |
| 22 | DRB*W602 | 279 (285) | DRB*W609 | 219 (223) | DRB6*0106 | 192 |

[a]Animals with Chinese,
[b]animals with Burmese origin.
[c]DRB1*1003 belong to haplotype 8 or 9;
( ) STR length observed in some (1-3) animals;
? STR not or rarely detected but presence of gene ascertained by sequencing;
205?, 175? STR's detected but not confirmed by sequencing

TABLE 2

HLA-DRB haplotypes defined by sequencing and D6S2878 genotyping

| | Haplotype | DRB1 locus | STR | 2nd DRB locus | STR | 3rd DRB locus | STR |
|---|---|---|---|---|---|---|---|
| DR8 | DR8a | DRB1*0801(03) | 170 (172) | | | | |
| | DR8b | DRB1*080302 | 176 | | | | |
| DR1 | DR1a/DR103 | DRB1*010101/0103 | 154 (156) | DRB6*010101 | 136 | | |
| | DR1b | DRB1*010201 | 160 | DRB6*0101 | 136 | | |
| | DR10 | DRB1*100101 | 161 | DRB6*0101 | 136 | | |
| DR52 | DR17a | DRB1*030101 | 172 | DRB3*010101(2) | 180 | | |
| | DR17b | DRB1*0301 | 178-184 | DRB3*0202(01 | 208 (206, 210) | | |
| | DR11a | DRB1*110101 | 182-192 | DRB3*020201 | 206-218 | | |
| | DR11b | DRB1*110201 | 186 | DRB3*020201 | 214 | | |
| | DR11c | DRB1*110401 | 188 | DRB3*020201 | 208 (210) | | |

TABLE 2-continued

HLA-DRB haplotypes defined by sequencing and D6S2878 genotyping

|  | Haplotype | DRB1 locus | STR | 2nd DRB locus | STR | 3rd DRB locus | STR |
|---|---|---|---|---|---|---|---|
|  | DR12a | DRB1*120101 | 200 | DRB3*010102 | 180 |  |  |
|  | DR12b | DRB1*1201 | 206 (208) | DRB3*02(0201) | 210, 212 |  |  |
|  | DR12c | DRB1*120201 | 216 | DRB3*030101 | 186 |  |  |
|  | DR13a | DRB1*1301(01) | 194 | DRB3*0101(02) | 180 |  |  |
|  | DR13b | DRB1*1301(01) | 194, 196 | DRB3*02(0201) | 204-214 |  |  |
|  | DR13c | DRB1*1302(01) | 188, 206-218 | DRB3*0301/0101 | 186 |  |  |
|  | DR14a | DRB1*140101 | 192 | DRB3*0211 | 212 |  |  |
|  | DR14b | DRB1*140101 | 186, 188, 196 | DRB3*020201 | 210 |  |  |
|  | DR14c | DRB1*140101 | 198 | DRB3*0201 | 214 |  |  |
| DR53 | DR4a | DRB1*0401(01) | 180, 182, 184 | DRB4*(010101) | 178, 180, (176, 182/4) | DRB7*010101 | 135 |
|  | DR4b | DRB1*0402 | 194 | DRB4*010101 | 176 | DRB7*010101 | 135 |
|  | DR4c | DRB1*0404 | 192 (196) | DRB4*010101 | 178 | DRB7*010101 | 135 |
|  | DR4d | DRB1*040701 | 184 | DRB4*010101 | 178 | DRB7*010101 | 135 |
|  | DR4e | DRB1*0408 | 180 | DRB4*010101 | 178 | DRB7*010101 | 135 |
|  | DR7 | DRB1*070101 | 149 | DRB4*010101 | 170, 176, 180 | DRB7*010101/2 | 135 |
|  | DR9 | DRB1*09(0102) | 170 (196) | DRB4*010101 | 180 | DRB7*010101 | 135 |
| DR51 | DR15a | DRB1*150101 | 186 | DRB5*0101(01) | 180 | DRB6*(0201) | 154 |
|  | DR15b | DRB1*150101 | 186, 190 (184, 188) | DRB5*0101(01) | 184 (190) | DRB6*(0201) | 152 |
|  | DR15c | DRB1*150201 | 202-208 | DRB5*0102 | 220 | DRB6*(0201) | 174 |
|  | DR16 | DRB1*160101 | 178 | DRB5*? | 184 | DRB6*0202 | 144 |

( ) indicates STR lengths detected only once or twice

TABLE 3

Gene frequencies and numbers (#) of Mamu- and HLA-DRB haplotypes tested by D6S2878

| Mamu hapl[a] | # | gf[b] (2n = 240) | HLA hapl[a] |  | # | gf[c] |
|---|---|---|---|---|---|---|
| 1a | 43 (4)[d] | 0,104 | DR8a |  | 5 (2)[d] | 0.039 |
| 1b | 4 | 0,004 | DR8b |  | 2 (2) |  |
| 2 | 20 (2) | 0,017 | DR1a | -DR103 | 42 (20) | 0.094 |
| 3 | 1 | 0,004 | DR1b |  | 8 (2) |  |
| 4 | 2 | 0,004 | DR10 |  | 4 | 0.013 |
| 5 | 2 | 0,004 | DR52 | -DR17a | 34 (16) | 0.111 |
| 6 | 2 | 0,004 |  | -DR17b | 12 (6) |  |
| 7 | 1 | 0,004 |  | -DR11a | 25 (2) |  |
| 8 | 3 | 0,004 |  | -DR11b | 2 (2) | 0.134 |
| 9 | 1 | 0,004 |  | -DR11c | 6 (6) |  |
| 10 | 4 | 0,008 |  | -DR12a | 1 |  |
| 11a | 32 | 0,063 |  | -DR12b | 5 (2) | 0.023 |
| 11b | 7 | 0,017 |  | -DR12c | 1 |  |
| 11a or b[e] |  | 0,083 |  | -DR13a | 13 (6) |  |
| 11c | 7 (4) | 0,004 |  | -DR13b | 16 (6) | 0.102 |
| 11d | 21 | 0,096 |  | -DR13c | 12 (4) |  |
| 12 | 58 (2) | 0,163 |  | -DR14a | 1 |  |
| 13 | 10 | 0,008 |  | -DR14b | 4 (2) | 0.032 |
| 14 | 7 (4) | 0,021 |  | -DR14c | 2 (2) |  |
| 15a | 7 (2) | 0,033 | DR53 | -DR4a | 23 (6) |  |
| 15b | 2 | 0,008 |  | -DR4b | 2 (2) |  |
| 16 | 3 | 0,029 |  | -DR4c | 11 (6) | 0.128 |
| 17 | 7 | 0,025 |  | -DR4d | 2 |  |
| 18a | 3 | 0,004 |  | -DR4e | 1 |  |
| 18b | 2 | 0,004 |  | -DR7 | 28 (12) | 0.132 |
| 19a | 5 | 0,071 |  | -DR9 | 10 (2) | 0.014 |
| 19b | 3 | 0,013 | DR51 | -DR15a1 | 5 |  |
| 20 | 1 | 0,008 |  | -DR15a2 | 39 (16) | 0.107 |
| 21a | 20 (2) | 0,050 |  | -DR15b | 4 (2) |  |
| 21b | 2 | 0,004 |  | -DR16 | 2 (2) | 0.036 |
| 22 | 14 (2) | 0,042 |  |  |  |  |
| other | n.t. | 0,092 | others |  | n.t. | 0.035 |
| total | 294 | 1,000 | total |  | 322 | 1.000 |

[a]Mhc-DRB haplotypes correspond to those defined in Table 1 and 2, respectively.
[b]Gene frequencies (gf) of Mamu-DRB haplotypes of the rhesus macaque breeding colony.
[c]Gene frequencies (gf) of caucasoid HLA-DRB haplotypes according to Marsh and coworkers (39).
[d]( ) refer to # of homozygous typing cells included in the total #.
[e]Haplotypes 9a and b could only be descriminated by D6S2878 genotyping and sequencing;
n.t. not tested.

TABLE 4

Patr-DRB haplotypes defined by exon 2 sequencing and DRB-STR genotyping

| hapl* | 1st DRB locus | STR | 2nd DRB locus | STR | 3rd DRB locus | STR | 4th DRB locus | STR | 5th DRB locus | STR |
|---|---|---|---|---|---|---|---|---|---|---|
| 1 | DRB1*0205 | 214 | DRB3*0214L | 182 |  |  |  |  |  |  |
| 2 | DRB4*0201 | 138 | DRB*W902 | 192, 194 |  |  |  |  |  |  |
| 3 | DRB1*02new | 228 | DRB3*0102L | 186 | DRB5*0101L | 170 |  |  |  |  |
| 4a | DRB1*0302 | 190 (184) | DRB3*0102 | 186 | DRB6*0305 | 155 |  |  |  |  |
| 4b | DRB1*0308 | 178 | DRB3*0102 | 186 | DRB6*0305 | 155 |  |  |  |  |
| 4c | DRB1*0309 | 176 | DRB3*0102 | 186 | DRB6*0305 | 155 |  |  |  |  |
| 5a | DRB1*0701 | 157 | DRB4*0104 | 186 | DRB7*0101 | 135 |  |  |  |  |
| 5b | DRB1*0702 | 153 | DRB4*0104 | 186 | DRB7*0101 | 135 |  |  |  |  |
| 6 | DRB1*1001 | 168 | DRB5*0310 | 174 | DRB6*0108 | 145 |  |  |  |  |
| 7 | DRB1*0309 | 176 | DRB6*0305 | 155 | DRB*W903 | 190 |  |  |  |  |

TABLE 4-continued

Patr-DRB haplotypes defined by exon 2 sequencing and DRB-STR genotyping

| hapl* | 1st DRB locus | STR | 2nd DRB locus | STR | 3rd DRB locus | STR | 4th DRB locus | STR | 5th DRB locus | STR |
|---|---|---|---|---|---|---|---|---|---|---|
| 8a | DRB1*0201 | 207, 211, 217 (209) | DRB3*0201 | 186 | DRB5*0301 | 174 | DRB6*0108 | 144 | | |
| 8b | DRB1*0201 | 209 | DRB3*0208 | 220 | DRB5*0306 | 174 | DRB6*0109 | 145 | | |
| 8c | DRB1*0201 | 209 | DRB3*0208 | 204 | DRB5*0304 | 174 | DRB6*0108 | 145 | | |
| 8d | DRB1*0202L | 226 | DRB3*0209L | 206 | DRB5*0306L | 195 | DRB6*0109 | 145 | | |
| 8e | DRB1*02new | 211 | DRB3*0208 | 212 | DRB5*0311 | 172 | DRB6*0109 | 145 | | |
| 8f | DRB1*0204 | 205 | DRB3*0201 | 188 | DRB5*0301 | 174 | DRB6*0108 | 144 | | |
| 8g | DRB1*0204 | 205 | DRB3*0208 | 208 | DRB5*0101L | 170 | DRB6*0109 | 145 | | |
| 8h | DRB1*0204 | 205 | DRB3*0208 | 208 (200) | DRB5*0102 | 170 | DRB6*0109 | 145 | | |
| 8i | DRB1*0204 | 205 | DRB3*0208 | 210 | DRB5*0102L | 170 | DRB6*0109 | 145 | | |
| 8j | DRB1*0204 | 221, 225 | DRB3*0208 | 212 | DRB5*0101L | 170 | DRB6*0109 | 145 | | |
| 9a | DRB1*0302 | 182 | DRB3*0102 | 186 | DRB5*0312 | 174 | DRB6*0305 | 155 | | |
| 9b | DRB1*0307 | 164, 174 | DRB3*0208 | 186 | DRB5*0301 | 174 | DRB6*0305 | 155 | | |
| 9c | DRB1*0307 | 166 | DRB3*0102 | 186 | DRB5*0306 | 174 | DRB6*0305 | 155 | | |
| 9d | DRB1*0307 | 172 | DRB3*0102 | 186 | DRB5*0102 | 170 | DRB6*0305 | 155 | | |
| 10 | DRB1*1001 | 170 | DRB3*0208 | 208 | DRB5*0310 | 174 | DRB6*0108 | 155 | | |
| 11 | DRB1*0311 | 184 | DRB3*0208 | 202 | DRB5*0307 | 174 | DRB*W901 | 190 | | |
| 12 | DRB1*0305 | 166, (168) | DRB3*0208 | 214, 218, 222, (208) | DRB5*0310 | 174 | DRB6*0108 | 145 | DRB6*03? | 155 |
| 13 | DRB1*0201 | 205 | DRB3*0208 | 202 | DRB5*0307 | 174 | DRB6*0108 | 145 | DRB6*0305 | 155 |

*Thirteen region configurations (1-13) could be defined. Letter surfixes (for example 7a-7k) indicate that a region configuration displays allelic polymorphism and can thus be split in different haplotypes.
Data in parentheses indicate STR lengths detected only once or twice

TABLE 5

Mafa-DRB haplotypes defined by exon 2 sequencing and DRB-STR genotyping

| hapl | 1st DRB locus | STR | 2nd DRB locus | STR | 3rd DRB locus | STR | 4th DRB locus | STR |
|---|---|---|---|---|---|---|---|---|
| 1 | DRB1*0306 | 193 | DRB5*0309 | 227 | DRB*W6501 | 225 | DRB6*0112 | 188 |
| 2 | DRB*W405 | 211 | DRB*W2504 | 209 | DRB6*0114 | 226 | | |
| 3 | DRB1*0309 | 209 | DRB*W2001 | 283 | DRB6*0107 | ? | | |
| 4 | DRB*W6601 | 193 | DRB*W2001 | 274 | DRB6*0108 | 204 | | |
| 5 | DRB1*0411 | 229 | DRB*W360202 | 229 | DRB6*0115 | 214 | | |
| 6 | DRB1*0312 | 247 (239, 251) | DRB*W2502 | 185 | DRB6*0107 | 208 | | |
| 7 | DRB1*0313 | 211 | DRB*W3601 | 227 | DRB6*0105 | 210 | DRB*W102? | 304 |
| 8 | DRB1*0314 | 181 | DRB1*0315 | 211 | DRB6*0112 | 176 | | |
| 9 | DRB1*0316 | 195 | DRB*W4001 | 203 | ? | 181? | | |
| 10 | DRB1*0317 | 193 (195) | DRB*W601 | 203 | DRB*W2001 | 274 | DRB*W6701 | 189 (195) |
| 11 | DRB1*0317 | 193 | DRB*W601 | 203 | DRB6*0106 | ? | | |
| 12 | DRB1*0401 | 189 | DRB5*0303 | 169 | DRB4*0102 | 231 | DRB6*011302 | 182 |
| 13 | DRB1*0401 | 189 (187) | DRB5*030101 | 169 | DRB*W303 | 247 | | |
| 14 | DRB1*0401 | 189 | DRB5*030101 | 169 | DRB4*0101? | 255, 259 | | |
| 15 | DRB1*0403 | 207 | DRB*W3701 | 241 | DRB6*011301 | ? | | |
| 16 | DRB1*0403 | 201 | DRB*W3701 | 225 | ? | | | |
| 17 | DRB1*0704 | 191 | DRB*W605 | 281 | DRB1*0308 | 234 | | |
| 18 | DRB1*0704 | ? | ? | | 172? | | DRB*W5301 | 219 |
| 19 | DRB1*1002 | 218, 208, (204) | DRB*W4901 | 259, 263, (265) | DRB6*0109 | 184 | | |
| 20 | DRB3*0401 | 239 | DRB5*0306 | 169 | DRB6*0110 | 186 | | |
| 21 | DRB*W6801 | 209 | DRB6*0111 | 178 | | | | |
| 22 | DRB*W2101 | 227 (229) | DRB6*0101 | 204 (206) | DRB*W501? | 189 (221) | | |

Data in parentheses are STR length observed in some (one or two) animals.
Question marks indicate STRs not detected or rarely detected but presence of gene ascertained by sequencing.
172?, 181? Indicate STRs detected but not confirmed by sequencing.
DRB4*0101? And DRB*W501? detected on cDNA, but not on gDNA most likely due to primer inconsistency.

TABLE 6

Mafa-DRB haplotypes of a cynomolgus family (FIG. 10) defined by exon 2 sequencing and DRB-STR typing

| hapl | 1st DRB locus | STR | 2nd DRB locus | STR | 3rd DRB locus | STR |
|---|---|---|---|---|---|---|
| a | DRB1*0403 | 201 | DRB*W3701 | 225 | ? | |
| b | DRB1*0704 | 191 | DRB*W605 | 281 | DRB1*0308 | 234 |
| c | DRB1*0312 | 247 (239, 251) | DRB*W2502 | 185 | DRB6*0107 | 208 |
| d | DRB1*0401 | 189 | DRB5*030101 | 169 | DRB4*0101? | 255, 259 |
| (e* | DRB5*0305) | | | | | |
| f | DRB1*0411 | 229 | DRB*W360202 | 229 | DRB6*0115 | 214 |

TABLE 6-continued

Mafa-DRB haplotypes of a cynomolgus family (FIG. 10) defined by exon 2 sequencing and DRB-STR typing

| hapl | 1st DRB locus | STR | 2nd DRB locus | STR | 3rd DRB locus | STR |
|---|---|---|---|---|---|---|
| g | DRB*W2101 | 227 (229) | DRB6*0101 | 204 (206) | DRB*W501? | 189 (221) |
| g* | DRB1*1002 | 218, 208, (204) | DRB*W4901 | 259, 263, (265) | DRB6*0109 | 184 |

Data in parentheses are STR length observed in some (one or two) animals.
Question marks indicate STRs not detected or rarely detected but presence of gene ascertained by sequencing.
172?, 181? Indicate STRs detected but not confirmed by sequencing.
DRB*W501? detected on cDNA, but not on gDNA most likely due to primer inconsistency.
*haplotype e only determined by cDNA typing

INCORPORATION OF SEQUENCE LISTING

Incorporated herein by reference in its entirety is the Sequence Listing for the application. The Sequence Listing is disclosed on a computer-readable ASCII text file entitled "Sequence_Listing_294-368_PCT_US.txt," created on Jan. 14, 2013. The sequence.txt file is 33.6 kilobytes in size.

The invention claimed is:

1. A method for detecting a DRB haplotype in a sample comprising nucleic acid from a primate cell, said method comprising:
amplifying the D6S2878 microsatellite from the nucleic acid, wherein said amplifying comprises contacting the nucleic acids with a primer pair selected from: a first primer consisting of SEQ ID NO: 1 and a second primer consisting of SEQ ID NO: 3; a first primer consisting of SEQ ID NO: 2 and a second primer consisting of SEQ ID NO: 4 or 5; and a first primer consisting of SEQ ID NO: 6 and a second primer consisting of SEQ ID NO: 3, 4 or 5;
detecting the length of the amplified microsatellite;
and correlating the detected length of the amplified microsatellite with the DRB haplotype in the sample, wherein the DRB haplotype is defined by the number of DRB genes and the specific DRB alleles of said DRB genes.

2. The method according to claim 1, wherein the correlating comprises comparing the detected microsatellite length with a reference.

3. The method according to claim 2, wherein said reference comprises a database of DRB haplotypes correlated with D6S2878 microsatellite lengths.

4. The method according to claim 3, wherein said database is present in an electronic storage device.

5. The method according to claim 1, wherein one or more of the primers is labelled.

6. The method according to claim 1, wherein the nucleic acid in the sample comprises genomic DNA.

7. The method according to claim 1, wherein the first primer consists of SEQ ID NO: 1; and the second primer consists of SEQ ID NO: 3.

8. The method according to claim 1, wherein the first primer consists of SEQ ID NO: 2; and the second primer consists of SEQ ID NO: 4 or 5.

9. The method according to claim 1, wherein the first primer consists of SEQ ID NO: 6; and the second primer consists of SEQ ID NO: 3, 4 or 5.

* * * * *

```
                        SEQUENCE LISTING

<160> NUMBER OF SEQ ID NOS: 147

<210> SEQ ID NO 1
<211> LENGTH: 19
<212> TYPE: DNA
<213> ORGANISM: Artificial
<220> FEATURE:
<223> OTHER INFORMATION: primer 5'HLA-DRB-STR_VIC

<400> SEQUENCE: 1
gagagcttca cagtgcagc                                                  19

<210> SEQ ID NO 2
<211> LENGTH: 21
<212> TYPE: DNA
<213> ORGANISM: Artificial
<220> FEATURE:
<223> OTHER INFORMATION: 5'Mamu-DRB-STR primer

<400> SEQUENCE: 2
ttcacagtgc agcggcgagg t                                               21

<210> SEQ ID NO 3
<211> LENGTH: 21
<212> TYPE: DNA
<213> ORGANISM: Artificial
<220> FEATURE:
<223> OTHER INFORMATION: 3'HLA-DRB-STR primer

<400> SEQUENCE: 3
gagaggattc taaatgctca c                                               21

<210> SEQ ID NO 4
<211> LENGTH: 20
<212> TYPE: DNA
<213> ORGANISM: Artificial
<220> FEATURE:
<223> OTHER INFORMATION: 3'Mamu-DRB-STR_VIC primer

<400> SEQUENCE: 4
acacctgtgc cctcagaact                                                 20

<210> SEQ ID NO 5
<211> LENGTH: 20
<212> TYPE: DNA
<213> ORGANISM: Artificial
```

```
<220> FEATURE:
<223> OTHER INFORMATION: 3'Mamu-DRB-STR_FAM_1007 primer

<400> SEQUENCE: 5
acatctgtgt cctcagacct                                              20

<210> SEQ ID NO 6
<211> LENGTH: 21
<212> TYPE: DNA
<213> ORGANISM: Artificial
<220> FEATURE:
<223> OTHER INFORMATION: 5'DRB-exon2 primer

<400> SEQUENCE: 6
cgtgtcccca cagcacgttt c                                            21

<210> SEQ ID NO 7
<211> LENGTH: 52
<212> TYPE: DNA
<213> ORGANISM: Homo sapiens

<400> SEQUENCE: 7
gtgtgtgtgt gtgtgtgtgt gtgtgtgtgt gtaagaaaga gagagagcgc gc          52

<210> SEQ ID NO 8
<211> LENGTH: 54
<212> TYPE: DNA
<213> ORGANISM: Homo sapiens

<400> SEQUENCE: 8
gtgtgtgtgt gtgtgtgtgt gtgtgtgtgt gtgtaagaaa gagagagagc gcgc        54

<210> SEQ ID NO 9
<211> LENGTH: 58
<212> TYPE: DNA
<213> ORGANISM: Homo sapiens

<400> SEQUENCE: 9
gtgtgtgtgt gtgtgtgtgt gtgtgtgtgt gtgtgtgtaa gaaagagaga gagcgcgc    58

<210> SEQ ID NO 10
<211> LENGTH: 58
<212> TYPE: DNA
<213> ORGANISM: Homo sapiens

<400> SEQUENCE: 10
ctctgtgtgt gtgtgtgtgt gtgtgtgtgt gtgtgtgaga gagagagaga gagcgcgc    58

<210> SEQ ID NO 11
<211> LENGTH: 48
<212> TYPE: DNA
<213> ORGANISM: Homo sapiens

<400> SEQUENCE: 11
gtgtgtgtgt gtgtgtgtgt gtgagagaga gagagagagc gagaccgc               48

<210> SEQ ID NO 12
<211> LENGTH: 68
<212> TYPE: DNA
<213> ORGANISM: Homo sapiens
```

<400> SEQUENCE: 12
gtgtgtgtgt gtgtgtgtgt gagagagaga gagagagagg aagagagaga cagaaagagg    60
gagcgcgc    68

<210> SEQ ID NO 13
<211> LENGTH: 90
<212> TYPE: DNA
<213> ORGANISM: Homo sapiens

<400> SEQUENCE: 13
gtgtgtgtgt gtgtgtgtgt gtgtgtgtgt gtgtgtgaga gagagagaga gagagagagg    60
ggaagagaga gacagaaaga gggagcgcgc    90

<210> SEQ ID NO 14
<211> LENGTH: 74
<212> TYPE: DNA
<213> ORGANISM: Homo sapiens

<400> SEQUENCE: 14
gtgtgtgtgt gtgtgtgtgt gtgtgtgtgt gtgtgtgaga gagagaggaa gagagagaca    60
gagagggagc gcgc    74

<210> SEQ ID NO 15
<211> LENGTH: 92
<212> TYPE: DNA
<213> ORGANISM: Homo sapiens

<400> SEQUENCE: 15
gtgtgtgtgt gtgtgtgtgt gtgtgtgtgt gtgtgtgtgt gtgtgtgtga gagagagaga    60
gagaggaaga gagagacaga gagggagcgc gc    92

<210> SEQ ID NO 16
<211> LENGTH: 116
<212> TYPE: DNA
<213> ORGANISM: Homo sapiens

<400> SEQUENCE: 16
gtgtgtgtgt gtgtgtgtgt gtgtgtgtgt gtgtgtgtgt gtgtgagaga gagagagaga    60
ggaagagaga gacagagaga gagagagagg aagagagaga cagagaggga gcgcgc    116

<210> SEQ ID NO 17
<211> LENGTH: 78
<212> TYPE: DNA
<213> ORGANISM: Homo sapiens

<400> SEQUENCE: 17
gtgtgtgtgt gtgtgtgtgt gtgtgtgtgt gagagagaga cagagagaga cagagagagg    60
aagagagaga gagagcgc    78

<210> SEQ ID NO 18
<211> LENGTH: 90
<212> TYPE: DNA
<213> ORGANISM: Homo sapiens

<400> SEQUENCE: 18
gtgtgtgtgt gtgtgtgtgt gtgtgtgtgt gtgtgtgtgt gagagagaga gacagagaga    60
gacagagaga ggaagagaga gagagagcgc    90

<210> SEQ ID NO 19
<211> LENGTH: 96
<212> TYPE: DNA
<213> ORGANISM: Homo sapiens

<400> SEQUENCE: 19
gtgtgtgtgt gtgtgtgtgt gtgtgtgtgt gtgtgtgtgt gtgtgagaca      60
gagagagaca gagagaggaa gagagagaga gagcgc                     96

<210> SEQ ID NO 20
<211> LENGTH: 106
<212> TYPE: DNA
<213> ORGANISM: Homo sapiens

<400> SEQUENCE: 20
gtgtgtgtgt gtgtgtgtgt gtgtgtgtgt gtgtgtgtgt gtgtgtgtgt      60
gtgtgagaca gagagagaca gagagaggaa gagagagaga gagcgc          106

<210> SEQ ID NO 21
<211> LENGTH: 72
<212> TYPE: DNA
<213> ORGANISM: Homo sapiens

<400> SEQUENCE: 21
gtgtgtgtgt gtgtgtgtgt gtgtgtgtgt gtgtgagaga gagagagaga gaggaagaga   60
gagagagagc gc                                               72

<210> SEQ ID NO 22
<211> LENGTH: 76
<212> TYPE: DNA
<213> ORGANISM: Homo sapiens

<400> SEQUENCE: 22
gtgtgtgtgt gtgtgtgtgt gtgtgtgtgt gtgtgtgtgt gtgagagaga gagagagaga   60
gagagagaga gagcgc                                           76

<210> SEQ ID NO 23
<211> LENGTH: 80
<212> TYPE: DNA
<213> ORGANISM: Homo sapiens

<400> SEQUENCE: 23
gtgtgtgtgt gtgtgtgtgt gtgtgtgtgt gtgtgtgtgt gtgtgagaga gagagagaga   60
gagagagaga gagagagcgc                                       80

<210> SEQ ID NO 24
<211> LENGTH: 82
<212> TYPE: DNA
<213> ORGANISM: Homo sapiens

<400> SEQUENCE: 24
gtgtgtgtgt gtgtgtgtgt gtgtgtgtgt gtgtgtgtgt gtgtgagaga gagagagaga   60
gagagagaga gagagagagc gc                                    82

<210> SEQ ID NO 25
<211> LENGTH: 90
<212> TYPE: DNA
<213> ORGANISM: Homo sapiens

<400> SEQUENCE: 25

```
gtgtgtgtgt gtgtgtgtgt gtgtgtgtgt gtgtgtgtgt gtgtgagaga gagagagaga    60
gagagagaga gagagagaga gagagagcgc                                      90
```

<210> SEQ ID NO 26
<211> LENGTH: 86
<212> TYPE: DNA
<213> ORGANISM: Homo sapiens

<400> SEQUENCE: 26

```
gtgtgtgtgt gtgtgtgtgt gtgtgtgtgt gtgtgtgaga gagagagaga                60
gagagagaga gagagagaga gagcgc                                          86
```

<210> SEQ ID NO 27
<211> LENGTH: 70
<212> TYPE: DNA
<213> ORGANISM: Homo sapiens

<400> SEQUENCE: 27

```
gtgtgtgtgt gtgtgtgtgt gtgtgtgtgt gtgtgagaga gagagacaga gagacagaga     60
gagagagcgc                                                            70
```

<210> SEQ ID NO 28
<211> LENGTH: 80
<212> TYPE: DNA
<213> ORGANISM: Homo sapiens

<400> SEQUENCE: 28

```
gtgtgtgtgt gtgtgtgtgt gtgtgtgtgt gtgtgagaga gagagacaga                60
gagacagaga gagagagcgc                                                 80
```

<210> SEQ ID NO 29
<211> LENGTH: 80
<212> TYPE: DNA
<213> ORGANISM: Homo sapiens

<400> SEQUENCE: 29

```
gtgtgtgtgt gtgtgtgtgt gtgtgtgtgt gtgtgagaga gagagagaga                60
gacagagaga gagagagcgc                                                 80
```

<210> SEQ ID NO 30
<211> LENGTH: 94
<212> TYPE: DNA
<213> ORGANISM: Homo sapiens

<400> SEQUENCE: 30

```
gtgtgtgtgt gtgtgtgtgt gtgtgtgtgt gtgtgtgtgt gtgtgtgtgt gtgtgagaga     60
gagagagaga gagagacaga gagagagaga gcgc                                 94
```

<210> SEQ ID NO 31
<211> LENGTH: 68
<212> TYPE: DNA
<213> ORGANISM: Homo sapiens

<400> SEQUENCE: 31

```
gtgtgtgtgt gtgtgtgtgt gtgtgtgtgt gtgtgtgaga gagagagaga cagagagaga     60
gagcgcgc                                                              68
```

<210> SEQ ID NO 32
<211> LENGTH: 72

```
<212> TYPE: DNA
<213> ORGANISM: Homo sapiens

<400> SEQUENCE: 32
gtgtgtgtgt gtgtgtgtgt gtgtgtgtgt gtgtgtgtgt gagagagaga gagacagaga    60
gagagagcgc gc                                                         72

<210> SEQ ID NO 33
<211> LENGTH: 74
<212> TYPE: DNA
<213> ORGANISM: Homo sapiens

<400> SEQUENCE: 33
gtgtgtgtgt gtgtgtgtgt gtgtgtgtgt gtgtgtgtgt gtgagagaga gagagacaga    60
gagagagagc gcgc                                                       74

<210> SEQ ID NO 34
<211> LENGTH: 98
<212> TYPE: DNA
<213> ORGANISM: Homo sapiens

<400> SEQUENCE: 34
gtgtgtgtgt gtgtgtgtgt gtgtgtgtgt gtgtgtgtgt gtgtgtgtgt gagagagaga    60
gagagagaga gacagagaga gagagagaga gagagcgc                             98

<210> SEQ ID NO 35
<211> LENGTH: 106
<212> TYPE: DNA
<213> ORGANISM: Homo sapiens

<400> SEQUENCE: 35
gtgtgtgtgt gtgtgtgtgt gtgtgtgtgt gtgtgtgtgt gtgtgtgtgt gtgtgtgtga    60
gagagagaga gagagagaga cagagagaga gagagagaga gagcgc                   106

<210> SEQ ID NO 36
<211> LENGTH: 110
<212> TYPE: DNA
<213> ORGANISM: Homo sapiens

<400> SEQUENCE: 36
gtgtgtgtgt gtgtgtgtgt gtgtgtgtgt gtgtgtgtgt gtgtgtgtgt gtgtgtgtgt    60
gtgtgagaga gagagagaga gagacagaga gagagagaga gagagagcgc               110

<210> SEQ ID NO 37
<211> LENGTH: 80
<212> TYPE: DNA
<213> ORGANISM: Homo sapiens

<400> SEQUENCE: 37
gtgtgtgtgt gtgtgtgtgt gtgtgtgtgt gtgtgagaga gagacagaga                60
gacagagaga gagagagcgc                                                 80

<210> SEQ ID NO 38
<211> LENGTH: 88
<212> TYPE: DNA
<213> ORGANISM: Homo sapiens

<400> SEQUENCE: 38
gtgtgtgtgt gtgtgtgtgt gtgtgtgtgt gtgtgtgtgt gtgtgtgtgt gtgagagaga    60
```

```
gacagagaga cagagagaga gagagcgc                                       88

<210> SEQ ID NO 39
<211> LENGTH: 86
<212> TYPE: DNA
<213> ORGANISM: Homo sapiens

<400> SEQUENCE: 39
gtgtgtgtgt gtgtgtgtgt gtgtgtgtgt gtgtgtgtgt gtgagagaga              60
gacagagaga cagagagaga gagcgc                                        86

<210> SEQ ID NO 40
<211> LENGTH: 86
<212> TYPE: DNA
<213> ORGANISM: Homo sapiens

<400> SEQUENCE: 40
gtgtgtgtgt gtgtgtgtgt gtgtgtgtgt gtgtgtgtgt gtgtgtgtga gagagagaga   60
cagagagaca gagagagaga gagcgc                                        86

<210> SEQ ID NO 41
<211> LENGTH: 90
<212> TYPE: DNA
<213> ORGANISM: Homo sapiens

<400> SEQUENCE: 41
gtgtgtgtgt gtgtgtgtgt gtgtgtgtgt gtgtgtgtgt gtgtgagaga gagagagaga   60
gagacagaga gacagagaga gagagagcgc                                    90

<210> SEQ ID NO 42
<211> LENGTH: 96
<212> TYPE: DNA
<213> ORGANISM: Homo sapiens

<400> SEQUENCE: 42
gtgtgtgtgt gtgtgtgtgt gtgtgtgtgt gtgtgtgtgt gtgtgtgtga gagagagaga   60
gagagagaga cagagagaca gagagagaga gagcgc                             96

<210> SEQ ID NO 43
<211> LENGTH: 86
<212> TYPE: DNA
<213> ORGANISM: Homo sapiens

<400> SEQUENCE: 43
gtgtgtgtgt gtgtgtgtgt gtgtgtgtgt gtgtgtgtgt gagagagaga gagagagaga   60
cagagagaca gagagagaga gagcgc                                        86

<210> SEQ ID NO 44
<211> LENGTH: 112
<212> TYPE: DNA
<213> ORGANISM: Homo sapiens

<400> SEQUENCE: 44
gtgtgtgtgt gtgtgtgtgt gtgtgtgtgt gtgtgtgtgt gtgtgtgtgt gtgtgtgtgt   60
gtgagagaga gagagagaga gagagacaga gagacagaga gagagagagc gc           112

<210> SEQ ID NO 45
<211> LENGTH: 106
<212> TYPE: DNA
```

```
<400> SEQUENCE: 45
gagtgtgtgt gtgtgtgtgt gtgtgtgtgt gtgtgtgaga gagagagaga        60
gagagagaga gagagaggaa gagagagaca gagagaggga gcgcgc           106

<210> SEQ ID NO 46
<211> LENGTH: 90
<212> TYPE: DNA
<213> ORGANISM: Homo sapiens

<400> SEQUENCE: 46
gagtgtgtgt gtgtgtgtgt gtgtgtgtgt gtgtgtgtga gagagagaga        60
ggaagagaga gacagagaga gggagcgcgc                              90

<210> SEQ ID NO 47
<211> LENGTH: 128
<212> TYPE: DNA
<213> ORGANISM: Homo sapiens

<400> SEQUENCE: 47
gagtgtgtgt gtgtgtgtgt gtgtgtgtgt gtgtgtgtgt gtgtgtgtgt        60
gagagagaga gagagagaga gagagagaga gagagagagg aagagagaga cagagagagg  120
gagcgcgc                                                     128

<210> SEQ ID NO 48
<211> LENGTH: 110
<212> TYPE: DNA
<213> ORGANISM: Homo sapiens

<400> SEQUENCE: 48
gagtgtgtgt gtgtgtgtgt gtgtgtgtgt gtgtgtgtga gagagagaga        60
gagagagaga gagagagaga ggaagagaga gacagagaga gggagcgcgc       110

<210> SEQ ID NO 49
<211> LENGTH: 76
<212> TYPE: DNA
<213> ORGANISM: Homo sapiens

<400> SEQUENCE: 49
gagagagtgt gtgtgtgtgt gtgtgtgtgt gtgagagaga gagagagaga ggaagagaca  60
gagagaggga gcgcgc                                             76

<210> SEQ ID NO 50
<211> LENGTH: 80
<212> TYPE: DNA
<213> ORGANISM: Homo sapiens

<400> SEQUENCE: 50
gagagagtgt gtgtgtgtgt gtgtgtgtgt gtgtgagaga gagagagaga gagaggaaga  60
gacagagaga gggagcgcgc                                         80

<210> SEQ ID NO 51
<211> LENGTH: 84
<212> TYPE: DNA
<213> ORGANISM: Homo sapiens

<400> SEQUENCE: 51
gagtgtgtgt gtgtgtatgt gtgtatgtgt gtgtgtgaga gagagagaca gagaggaaga  60
```
gagagacaga gagagggagc gcgc                                          84

<210> SEQ ID NO 52
<211> LENGTH: 64
<212> TYPE: DNA
<213> ORGANISM: Homo sapiens

<400> SEQUENCE: 52
gtatgtgtgt gtgtgtgtgt gtgagagaga gagagagaga cagaggaaga gagagagagc   60
gtgc                                                                64

<210> SEQ ID NO 53
<211> LENGTH: 86
<212> TYPE: DNA
<213> ORGANISM: Homo sapiens

<400> SEQUENCE: 53
gtatgtgtgt gtgtgtgtgt gtgtgtgaga gagagagaga gagagagaga gagacagaca   60
gaggaagaga gagagagcgt gtgcgc                                        86

<210> SEQ ID NO 54
<211> LENGTH: 36
<212> TYPE: DNA
<213> ORGANISM: Homo sapiens

<400> SEQUENCE: 54
gtctgtgtgt gtgtgtgaga gagagagaga gagaga                             36

<210> SEQ ID NO 55
<211> LENGTH: 48
<212> TYPE: DNA
<213> ORGANISM: Homo sapiens

<400> SEQUENCE: 55
gtgtgtgtgt gtgtgtgtgt gtgtgtgaga gagagagaga gagagaga                48

<210> SEQ ID NO 56
<211> LENGTH: 76
<212> TYPE: DNA
<213> ORGANISM: Homo sapiens

<400> SEQUENCE: 56
gtgtgtgtgt gtgtgtgtgt gtgtgtgtgt gtgtgtgtgt gtgtgtgtga gagagagaga   60
gagagagaga gagaga                                                   76

<210> SEQ ID NO 57
<211> LENGTH: 42
<212> TYPE: DNA
<213> ORGANISM: Homo sapiens

<400> SEQUENCE: 57
gtgtgtgtgt gtgtgtgtgt gtgtgtgtgt gagagagaga ga                      42

<210> SEQ ID NO 58
<211> LENGTH: 35
<212> TYPE: DNA
<213> ORGANISM: Homo sapiens

<400> SEQUENCE: 58
gtgtttgtgt gttgagagag agacacacac acaca                              35

```
<210> SEQ ID NO 59
<211> LENGTH: 35
<212> TYPE: DNA
<213> ORGANISM: Homo sapiens

<400> SEQUENCE: 59
gtgtttgtgt gttgagagag agagacacac acaca                                35

<210> SEQ ID NO 60
<211> LENGTH: 94
<212> TYPE: DNA
<213> ORGANISM: Macaca mulatta

<400> SEQUENCE: 60
gtgtgtgtct gtgtgtgtgt gtgtgtgtgt gtgtgagaga gagagagaga gagagagaga    60
gagagagaga gaggaagaca gagagcgcgc gcgc                                 94

<210> SEQ ID NO 61
<211> LENGTH: 96
<212> TYPE: DNA
<213> ORGANISM: Macaca mulatta

<400> SEQUENCE: 61
gtgtgtgtct gtgtgtgtgt gtgtgtgtgt gtgtgagaga gagagagaga gagagagaga    60
gagagagaga gagaggaaga cagagagcgc gcgcgc                               96

<210> SEQ ID NO 62
<211> LENGTH: 72
<212> TYPE: DNA
<213> ORGANISM: Macaca mulatta

<400> SEQUENCE: 62
gtgtgtgtgt gtgtgtgtgt gtgtgtgtgt gtgtgtgtgt gtgaaagaga gagagagcga    60
gcgagcgaga gc                                                         72

<210> SEQ ID NO 63
<211> LENGTH: 84
<212> TYPE: DNA
<213> ORGANISM: Macaca mulatta

<400> SEQUENCE: 63
gtgtgtgtgt gtgtgtgtgt gtgtgtgtgt gtgtgtgtgt gtgtgtgtgt gtgtgaaaga    60
gagagagagc gagcgagcga gagc                                            84

<210> SEQ ID NO 64
<211> LENGTH: 68
<212> TYPE: DNA
<213> ORGANISM: Macaca mulatta

<400> SEQUENCE: 64
gtgtgtgtgt gtgtgtgtgt gtgtgtgtgt gtgagacaga gagagagaga gggagagaga    60
gagcgcgc                                                              68

<210> SEQ ID NO 65
<211> LENGTH: 74
<212> TYPE: DNA
<213> ORGANISM: Macaca mulatta

<400> SEQUENCE: 65
gtgtgtgtgt gagtgtgtgt gtgtgtgtgt gtgtgtgtga gacagagaga gagagaggga    60
```

```
gagagagagc gcgc                                                    74

<210> SEQ ID NO 66
<211> LENGTH: 76
<212> TYPE: DNA
<213> ORGANISM: Macaca mulatta

<400> SEQUENCE: 66
gtgtgtgtgt gtgtgtgtgt gtgtgtgtgt gtgtgtgtgt gtgacagaga gagagagagg  60
gagagagaga gagcgc                                                  76

<210> SEQ ID NO 67
<211> LENGTH: 60
<212> TYPE: DNA
<213> ORGANISM: Macaca mulatta

<400> SEQUENCE: 67
gtgtgtgtct gtgtgtgtgt gtgtgtgtgt gtgagagaga gagagagaga gagagagagc  60

<210> SEQ ID NO 68
<211> LENGTH: 40
<212> TYPE: DNA
<213> ORGANISM: Macaca mulatta

<400> SEQUENCE: 68
gtgtgagaaa gaaagagaaa gaaagagaga gagcgcgcgc                        40

<210> SEQ ID NO 69
<211> LENGTH: 44
<212> TYPE: DNA
<213> ORGANISM: Macaca mulatta

<400> SEQUENCE: 69
gtgtgagaaa aagagaaaga gaaagaaaga gagagagtgc gcgc                   44

<210> SEQ ID NO 70
<211> LENGTH: 22
<212> TYPE: DNA
<213> ORGANISM: Macaca mulatta

<400> SEQUENCE: 70
gtgtaagaaa gagagcgtgc gc                                           22

<210> SEQ ID NO 71
<211> LENGTH: 40
<212> TYPE: DNA
<213> ORGANISM: Macaca mulatta

<400> SEQUENCE: 71
gtgtgagaaa gagagagaga gaggaagaga gagcgcgcgc                        40

<210> SEQ ID NO 72
<211> LENGTH: 132
<212> TYPE: DNA
<213> ORGANISM: Macaca mulatta

<400> SEQUENCE: 72
gtgtgtctgt gagtgtgtgt gtgtgtgtgt gtgtgtgtgt gtgagagaga gtgtgtgtgt  60
gtgtgtgtgt gtgagagaga gacagagaga cagagagaca gagagagaga gacagagaca 120
gagagagcgc gc                                                     132
```

<210> SEQ ID NO 73
<211> LENGTH: 134
<212> TYPE: DNA
<213> ORGANISM: Macaca mulatta

<400> SEQUENCE: 73
gtgtgtctgt gagtgtgtgt gtgtgtgtgt gtgtgtgtgt gtgtgagaga gagtgtgtgt      60
gtgtgtgtgt gtgtgagaga gagagacaga gacagagaga cagagagaga gagacagaga     120
cagagagagc gcgc                                                       134

<210> SEQ ID NO 74
<211> LENGTH: 70
<212> TYPE: DNA
<213> ORGANISM: Macaca mulatta

<400> SEQUENCE: 74
gtgtgtgtgt gtgtgtgtga gagtgtgtgt gggggggggga gggggagaga gagagggaga      60
gagcgcgcgc                                                              70

<210> SEQ ID NO 75
<211> LENGTH: 84
<212> TYPE: DNA
<213> ORGANISM: Macaca mulatta

<400> SEQUENCE: 75
gtgtgtgtgt gtgtgtgtgt gtgtgtgtgt gtgtgtgtga gagagagaga gagagagaga      60
gagagagaga gagagagaga gcgc                                              84

<210> SEQ ID NO 76
<211> LENGTH: 80
<212> TYPE: DNA
<213> ORGANISM: Macaca mulatta

<400> SEQUENCE: 76
gtgtgtgtgt gtgtgtgtgt gtgtgtgtgt gtgtgtgtgt gtgtgagaga gagagagaga      60
gagagagaga gagagagcgc                                                   80

<210> SEQ ID NO 77
<211> LENGTH: 64
<212> TYPE: DNA
<213> ORGANISM: Macaca mulatta

<400> SEQUENCE: 77
gtgtgtgtgt aagagtgtgt gtgtgtgtgt gtgtgtgaga gagagagaga gagagagaga      60
gagc                                                                    64

<210> SEQ ID NO 78
<211> LENGTH: 74
<212> TYPE: DNA
<213> ORGANISM: Macaca mulatta

<400> SEQUENCE: 78
gtgtgtgtgt gagtgtgtgt cagagagaga gagagagaga cagagacaga gagagagaca      60
gagacagagc gcgc                                                         74

<210> SEQ ID NO 79
<211> LENGTH: 108
<212> TYPE: DNA
<213> ORGANISM: Macaca mulatta -continued

<400> SEQUENCE: 79
gtgtgtgtgt gagtgtgtgt gagtgtgtgt gagtgtgtgt gtgtgtgtgt gtgtgtcaga     60
gagagagaga gagacagaga cagagagaga gacagagaca gagcgcgc                 108

<210> SEQ ID NO 80
<211> LENGTH: 152
<212> TYPE: DNA
<213> ORGANISM: Macaca mulatta

<400> SEQUENCE: 80
gtgtgtgtgt gagtgtgtgt gtgtgtgtgt gagagtgtgt gtctgtgtgt gtgtgtgagt     60
gtgagtgtgt gtatgtgaga gagagagaga gagagagaca gagacagaga cagagacaga   120
gacagagaca gagacagaga gagagcgcgc gc                                 152

<210> SEQ ID NO 81
<211> LENGTH: 146
<212> TYPE: DNA
<213> ORGANISM: Macaca mulatta

<400> SEQUENCE: 81
gtgtgtgtgt gagtgtgtgt gtgtgagagt gtgtgtctgt gtgtgtgtgt gagtgtgagt     60
gtgtgtatgt gagagagaga gagagagaga gagagagaga gagagagaga gagagacaga   120
gacagagaca gagagagagc gcgcgc                                         146

<210> SEQ ID NO 82
<211> LENGTH: 62
<212> TYPE: DNA
<213> ORGANISM: Macaca mulatta

<400> SEQUENCE: 82
gtgtgtgtgt gtgtgtgtgt gtgtgtgaga gagagagaga gagagagaga gagagagaga     60
gc                                                                    62

<210> SEQ ID NO 83
<211> LENGTH: 80
<212> TYPE: DNA
<213> ORGANISM: Macaca mulatta

<400> SEQUENCE: 83
gtgtgtgtgt gtgtgtgtgt gtgagtgtgt gtgtgagaga gagagagaga gagagagaga     60
gagagagaga gagagagagc                                                 80

<210> SEQ ID NO 84
<211> LENGTH: 80
<212> TYPE: DNA
<213> ORGANISM: Macaca mulatta

<400> SEQUENCE: 84
gtgtgtgtgt gtgtgtgtgt gtgtgtgtgt gtgtgtgtgt gagagagaga gagagagaga     60
gagagagaga gagagagagc                                                 80

<210> SEQ ID NO 85
<211> LENGTH: 102
<212> TYPE: DNA
<213> ORGANISM: Macaca mulatta

<400> SEQUENCE: 85
gtgtgtgtgt gtgtgtgtgt gtgtgtgtgt gtgtgtgtgt gtgagagaga gagagagaga     60

```
gagagagaga gagagagaga gagagagaga gagagagaga gc                          102

<210> SEQ ID NO 86
<211> LENGTH: 68
<212> TYPE: DNA
<213> ORGANISM: Macaca mulatta

<400> SEQUENCE: 86
gtgtgtgtgt gtgtgtgtgt gtgtgtgtgt gtgtgtgaga gagagagaga gagagagaga      60
gagagagc                                                                68

<210> SEQ ID NO 87
<211> LENGTH: 84
<212> TYPE: DNA
<213> ORGANISM: Macaca mulatta

<400> SEQUENCE: 87
gtgtgtgtgt gtgtgtgtgt gtgtgtgtgt gtgtgtgtga gagagagaga gagagagaga      60
gagagagaga gagagagaga gagc                                              84

<210> SEQ ID NO 88
<211> LENGTH: 68
<212> TYPE: DNA
<213> ORGANISM: Macaca mulatta

<400> SEQUENCE: 88
gtgtgtgtgt gtgtgtgtgt gtgtgtgtga gagagagaga gagagagaga gagagagaga      60
gagagcgc                                                                68

<210> SEQ ID NO 89
<211> LENGTH: 98
<212> TYPE: DNA
<213> ORGANISM: Macaca mulatta

<400> SEQUENCE: 89
gtgtgtgtgt gtgtgtgtgt gtgtgtgtgt gtgtgtgtgt gagagagaga gagacagaga      60
gagacagaga gagagagaca gagacagaga gagcgcgc                               98

<210> SEQ ID NO 90
<211> LENGTH: 98
<212> TYPE: DNA
<213> ORGANISM: Macaca mulatta

<400> SEQUENCE: 90
gtgtgtgtgt gtgtgtgtgt gtgtgtgtgt gtgtgtgtgt gtgagagaga gagagagaga      60
gagagagaca gagagacaga cagagagaga gagagcgc                               98

<210> SEQ ID NO 91
<211> LENGTH: 90
<212> TYPE: DNA
<213> ORGANISM: Macaca mulatta

<400> SEQUENCE: 91
gtgtgtgtgt gtgtgtgtgt gtgtgtgtgt gtgtgagaga gagagagaga gagagagaga      60
cagagagaca gacagagaga gagagagcgc                                        90

<210> SEQ ID NO 92
<211> LENGTH: 106
<212> TYPE: DNA
```

<213> ORGANISM: Macaca mulatta

<400> SEQUENCE: 92
gtgtgtgtgt gtgtgtgtgt gtgtgtgtgt gtgagagaga gagagagaga    60
gagagagaga gacagagaga gagacagaga cagagagagc gcgcgt    106

<210> SEQ ID NO 93
<211> LENGTH: 64
<212> TYPE: DNA
<213> ORGANISM: Macaca mulatta

<400> SEQUENCE: 93
gagagagaga gagagagaga gagagagaga gagagagaga gagagagaga gagagagaga    60
gcgc    64

<210> SEQ ID NO 94
<211> LENGTH: 38
<212> TYPE: DNA
<213> ORGANISM: Macaca mulatta

<400> SEQUENCE: 94
gagtgtgtgt gtgtgtgtgt gtgagagaga gagagcgc    38

<210> SEQ ID NO 95
<211> LENGTH: 64
<212> TYPE: DNA
<213> ORGANISM: Macaca mulatta

<400> SEQUENCE: 95
gagtgtgtgt gtgtgtctgt gtgtgtgtgt gtttgtgtgt gtgtatgtga gagagagaga    60
gagc    64

<210> SEQ ID NO 96
<211> LENGTH: 40
<212> TYPE: DNA
<213> ORGANISM: Macaca mulatta

<400> SEQUENCE: 96
gagtatgtgt gtgtgtgtga gagagagaga gagagagcgc    40

<210> SEQ ID NO 97
<211> LENGTH: 42
<212> TYPE: DNA
<213> ORGANISM: Macaca mulatta

<400> SEQUENCE: 97
gagtatgtgt gtgtgtgtga gagagagaga gagagagagc gc    42

<210> SEQ ID NO 98
<211> LENGTH: 78
<212> TYPE: DNA
<213> ORGANISM: Macaca mulatta

<400> SEQUENCE: 98
gagtgtgtgt gtgtgtctgt gtgtgtgtgt atgtgagaga gagagagaga gagagagaga    60
gagagagaga aagcgcgc    78

<210> SEQ ID NO 99
<211> LENGTH: 52
<212> TYPE: DNA
<213> ORGANISM: Macaca mulatta

<400> SEQUENCE: 99
gagtgtgtgt gtgtctgtgt gtgtgtgtat gtgagagaga gagagagagc gc    52

<210> SEQ ID NO 100
<211> LENGTH: 56
<212> TYPE: DNA
<213> ORGANISM: Macaca mulatta

<400> SEQUENCE: 100
gagtgtgtgt gtgtgtatct gtgtgtgtgt gtatgtgaga gagagagaga gagcgc    56

<210> SEQ ID NO 101
<211> LENGTH: 90
<212> TYPE: DNA
<213> ORGANISM: Macaca mulatta

<400> SEQUENCE: 101
gagtgtgtgt gtgtgtctgt gtgtgtgtgt gtgtgtgtga gagagagaga gagagagaga    60
gagagagaga gagagaggga gagagagcgc    90

<210> SEQ ID NO 102
<211> LENGTH: 80
<212> TYPE: DNA
<213> ORGANISM: Macaca mulatta

<400> SEQUENCE: 102
gagtgtgtgt gtgtgtctgt gtgtgtgtgt gtgtgtgtgt gtgagagaga gagagagaga    60
gagagaggga gagagagcgc    80

<210> SEQ ID NO 103
<211> LENGTH: 66
<212> TYPE: DNA
<213> ORGANISM: Macaca mulatta

<400> SEQUENCE: 103
gtgtgtgtgt gtgtgtgtgt gtgtgtgtgt gtgtgtgtgt gtgtgtgtgt gtgtgtgaga    60
gagagc    66

<210> SEQ ID NO 104
<211> LENGTH: 84
<212> TYPE: DNA
<213> ORGANISM: Macaca mulatta

<400> SEQUENCE: 104
gtgtgtgtgt gtgtgtgtgt gtgtgtgaga gagagagaga gagacagaga gacagagaga    60
gagagagaga cagagagaga gagc    84

<210> SEQ ID NO 105
<211> LENGTH: 86
<212> TYPE: DNA
<213> ORGANISM: Macaca mulatta

<400> SEQUENCE: 105
gtgtgtgtgt gtgtgtgtgt gtgtgtgtgt gtgtgtgtgt gtgtgagaga gagagagaga    60
gagagagaga gagagagaga gagagc    86

<210> SEQ ID NO 106
<211> LENGTH: 54
<212> TYPE: DNA

<213> ORGANISM: Macaca mulatta

<400> SEQUENCE: 106
gtgtgtgtgt gtgtgtgtgt gtgtgtgtgt gtgtgagaga gagagagaga gagc     54

<210> SEQ ID NO 107
<211> LENGTH: 80
<212> TYPE: DNA
<213> ORGANISM: Macaca mulatta

<400> SEQUENCE: 107
gtgtgtgtgt gtgtgtgtgt gtgtgtgtgt gtgtgtgaga gagagagaga gagagagaga     60
gagagagaga gagagagagc     80

<210> SEQ ID NO 108
<211> LENGTH: 92
<212> TYPE: DNA
<213> ORGANISM: Macaca mulatta

<400> SEQUENCE: 108
gagtgtgtgt gtgtgtctgt gtgtgtgtgt gtgtgtgtgt gtgtgtgaga gagagagaga     60
gagagagaga gagagagaga gagagaaaga gc     92

<210> SEQ ID NO 109
<211> LENGTH: 48
<212> TYPE: DNA
<213> ORGANISM: Macaca mulatta

<400> SEQUENCE: 109
gtgtgtgtgt gtgtgtgtgt gtgtgtgtgt atgagagaga gagagcgc     48

<210> SEQ ID NO 110
<211> LENGTH: 50
<212> TYPE: DNA
<213> ORGANISM: Macaca mulatta

<400> SEQUENCE: 110
gtgtgtgtgt gtgtgtgtgt gtgtgtgtgt gtatgagaga gagagagcgc     50

<210> SEQ ID NO 111
<211> LENGTH: 88
<212> TYPE: DNA
<213> ORGANISM: Macaca mulatta

<400> SEQUENCE: 111
gtgtgtgtgt gtgtgtgtgt gtgtgtgtgt gtgtgtgtgt gtgtgagaga gagagagaga     60
gagagagaga gagagagaga gagagagc     88

<210> SEQ ID NO 112
<211> LENGTH: 46
<212> TYPE: DNA
<213> ORGANISM: Macaca mulatta

<400> SEQUENCE: 112
gtgtgtgtgt gtgtgtgtgt gagagagaga gagagagaga gagagc     46

<210> SEQ ID NO 113
<211> LENGTH: 62
<212> TYPE: DNA
<213> ORGANISM: Macaca mulatta

<400> SEQUENCE: 113

```
gtgtgtgtgt gtgtgtgtgt gtgtgtgtgt gtgagagaga gagagagaga gagagagaga        60
gc                                                                       62

<210> SEQ ID NO 114
<211> LENGTH: 60
<212> TYPE: DNA
<213> ORGANISM: Macaca mulatta

<400> SEQUENCE: 114
gtgtgtgtgt gtgtgtgtgt gtgtgtgtgt gagagagaga gagagagaga gagagagcgc        60

<210> SEQ ID NO 115
<211> LENGTH: 170
<212> TYPE: DNA
<213> ORGANISM: Macaca mulatta

<400> SEQUENCE: 115
gtgtgtgtct gtgtgtctgt gtgtgtgtgt gtgtgtgtgt ctgtgtgtgt gtgtctgtgt        60
gtgtctgtgt ctgtgtgtgt gtgtctgtgt gtgtgtgtgt gtctgtgtgt gtgtgtctgt       120
gtgtgtgtgt gtgtgtgaga gagagagaga gagagagaga gagagagcgc                  170

<210> SEQ ID NO 116
<211> LENGTH: 88
<212> TYPE: DNA
<213> ORGANISM: Macaca mulatta

<400> SEQUENCE: 116
gagagtgtgt gtgtgtgtgt gtgtgtgtga gagagagaga cagagagaga gaaagagaga        60
gagagagaga cagagacaga gagcgcgc                                           88

<210> SEQ ID NO 117
<211> LENGTH: 58
<212> TYPE: DNA
<213> ORGANISM: Macaca mulatta

<400> SEQUENCE: 117
gtgtgtgtgt gtgtgtgtgt gagagagaga gagagagaga gagagagaga gagagagc          58

<210> SEQ ID NO 118
<211> LENGTH: 84
<212> TYPE: DNA
<213> ORGANISM: Macaca mulatta

<400> SEQUENCE: 118
gtgtgtgtgt gtgtgtgtgt gtgtgtgtgt gtgtgtgtgt gagagagaga gagagagaca        60
gacagagaca gagagagaga gcgc                                               84

<210> SEQ ID NO 119
<211> LENGTH: 86
<212> TYPE: DNA
<213> ORGANISM: Macaca mulatta

<400> SEQUENCE: 119
gtgtgtgtgt gtgtgtgtgt gtgtgtgtgt gtgtgtgtgt gtgagagaga gagagagaga        60
cagacagaga cagagagaga gagcgc                                             86

<210> SEQ ID NO 120
<211> LENGTH: 68
<212> TYPE: DNA
```

<213> ORGANISM: Macaca mulatta

<400> SEQUENCE: 120
gtgtgtgtct gtgtgtgtgt gtgtgagtgt gtgtgtgtga gacagagaga gagagagaga    60
gagagcgt    68

<210> SEQ ID NO 121
<211> LENGTH: 82
<212> TYPE: DNA
<213> ORGANISM: Macaca mulatta

<400> SEQUENCE: 121
gtgtgtgtct gtgtgtgtgc atgtgtgtgt gtgtgtgaga gagagagaga gagagagaca    60
gagagagaga gagagagagc gc    82

<210> SEQ ID NO 122
<211> LENGTH: 94
<212> TYPE: DNA
<213> ORGANISM: Macaca mulatta

<400> SEQUENCE: 122
gtgtgtgtgt gtgtgtgtgt gtgtgtgtgt gtgtgagaga gagagagaga aagagagaca    60
gagagagaga cagagagaga gacagagcgc gcgc    94

<210> SEQ ID NO 123
<211> LENGTH: 98
<212> TYPE: DNA
<213> ORGANISM: Macaca mulatta

<400> SEQUENCE: 123
gtgtgtgtgt gtgtgtgtgt gtgtgtgtgt gtgtgtgaga gagagagaga gagaaagaga    60
gacagagaga gagacagaga gagagacaga gcgcgcgc    98

<210> SEQ ID NO 124
<211> LENGTH: 54
<212> TYPE: DNA
<213> ORGANISM: Macaca mulatta

<400> SEQUENCE: 124
gtgtgtgtgt gtgtgtgtgt gtgtgagaga gagagagaga gagagagcga gcgc    54

<210> SEQ ID NO 125
<211> LENGTH: 112
<212> TYPE: DNA
<213> ORGANISM: Macaca mulatta

<400> SEQUENCE: 125
gtgtgtgtgt gtgtgcgtgt gtgtgtgtgt gtgtgtgtgt gtgtgtgtgt gagagagaga    60
gagagacaga gacagagaga cagagagaga gacagagaca gagagagcgc gc    112

<210> SEQ ID NO 126
<211> LENGTH: 92
<212> TYPE: DNA
<213> ORGANISM: Macaca mulatta

<400> SEQUENCE: 126
gtgtgtgtgt gtgtgtgtgt gtgtgtgtgt gtgtgtgtga gagagagaga gagagagaga    60
gagagacaga gacagagaca gagacagaga gc    92

```
<210> SEQ ID NO 127
<211> LENGTH: 112
<212> TYPE: DNA
<213> ORGANISM: Macaca mulatta

<400> SEQUENCE: 127
gtgtgtgtgt gtgtgtgtgt gtgtgtgtgt gtgtgtgtgt gagagagaga          60
gagagagaga gagagagaga gagagacaga gacagagaca gagacagaga gc       112

<210> SEQ ID NO 128
<211> LENGTH: 78
<212> TYPE: DNA
<213> ORGANISM: Macaca mulatta

<400> SEQUENCE: 128
gagtgtgtgt gtgtgtgtgt gtgtgtgtgt gtgtgtgtgt gagagagaga gagagagaga   60
gagagagaga gagagcgc                                              78

<210> SEQ ID NO 129
<211> LENGTH: 94
<212> TYPE: DNA
<213> ORGANISM: Macaca mulatta

<400> SEQUENCE: 129
gagtgtgtgt gtgtgtgtgt gtgtgtgtgt gtgtgtgtgt gtgtgagaga gagagagaga   60
gagagagaga gagagagaga gagagagaga gcgc                            94

<210> SEQ ID NO 130
<211> LENGTH: 70
<212> TYPE: DNA
<213> ORGANISM: Macaca mulatta

<400> SEQUENCE: 130
gtgtgtgtgt gtgtgtgtgt gtgtgtgtgt gtgtgtgtgt gtcagagaga gagagagaga   60
gagagagcgc                                                       70

<210> SEQ ID NO 131
<211> LENGTH: 66
<212> TYPE: DNA
<213> ORGANISM: Macaca mulatta

<400> SEQUENCE: 131
gtgtgtgtgt gagtgtgtgt gtgtgagtgt gtgtgtgagt gtgtgtgtgt gagagagaga   60
gagagc                                                           66

<210> SEQ ID NO 132
<211> LENGTH: 70
<212> TYPE: DNA
<213> ORGANISM: Macaca mulatta

<400> SEQUENCE: 132
gtgtgtgtgt gtgtgagtgt gtgtgtgtga gtgtgtgtgt gagtgtgtgt gtgagagaga   60
gagagagagc                                                       70

<210> SEQ ID NO 133
<211> LENGTH: 100
<212> TYPE: DNA
<213> ORGANISM: Macaca mulatta

<400> SEQUENCE: 133
```

```
gtgtgtgtgt gagtgtgtgt gtgtgtgtgt gtgtgtgtgt ctgagagaga gacagagaca    60
gagagacaga gagagagaca gagacagaga gagcccgcgc                         100

<210> SEQ ID NO 134
<211> LENGTH: 96
<212> TYPE: DNA
<213> ORGANISM: Macaca mulatta

<400> SEQUENCE: 134
gtgtgtgtgt gagtgtgtgt gagtgtgtgt gtgtgtgaga gagagagaca gagacagaga    60
gacagagaga gagacagaga cagagagagc ccgcgc                              96

<210> SEQ ID NO 135
<211> LENGTH: 254
<212> TYPE: DNA
<213> ORGANISM: Homo sapiens

<400> SEQUENCE: 135
cctggagcag aggcgggccg cggtggacac ctactgcaga cacaactacg ggttggtga    60 gagcttcaca gtgcagtgca gcggcgaggt gagcgcggcg cggggcgggg cctgagtccc   120
tgtaagcgga gaatctgagt gtgtgtgtgt gtgtgtgtgt gtgtgtgtgt gtgtaagaaa   180
gagagagagc gcgccatctg tgagcattta gaatcctctc aatccccagc aagcagttct   240
gagagcacag gtgt                                                     254

<210> SEQ ID NO 136
<211> LENGTH: 250
<212> TYPE: DNA
<213> ORGANISM: Homo sapiens

<400> SEQUENCE: 136
cctggaagac gagcgggccg cggtggacac ctactgcaga cacaactacg ggttggtga    60 gagcttcaca gtgcagtgca gcggcgaggt gagcgcggcg cggggcgggg cctgagtccc   120
tgtaagcgga gaatctgagt gtgtgtgtgt gtgtgtgtgt gtgtgtgtgt aagaaagaga   180
gagagcgcgc catctgtgag catttagaat cctctcaatc cccagcaagc agttctgaga   240
gcacaggtgt                                                          250

<210> SEQ ID NO 137
<211> LENGTH: 263
<212> TYPE: DNA
<213> ORGANISM: Homo sapiens

<400> SEQUENCE: 137
cctggagcag aagcgggccg cggtggacac ctactgcaga cacaactacg ggttggtga    60 gagcttcaca gtgcagtgca gcggcgaggt gagcgcggcg cggggcgggg cctgagtccc   120
tgtgagcgga gaatctgagt gtgtgtgtgt gtgtgtgtgt gtgtgtgtgt gtgtgtgtgt   180
gtgagagaga gagagagaga gagagagaga gagagcgcca tctgtgagca tttagaatcc   240
tctctatcct gagcaaggag ttc                                           263

<210> SEQ ID NO 138
<211> LENGTH: 285
<212> TYPE: DNA
<213> ORGANISM: Homo sapiens

<400> SEQUENCE: 138
cctggaggag aggcgggccg aggtggacac ctattgcaga cacaactacg ggttgtgga    60
```

```
gagcttcaca gtgcagtgca gcggcgaggt gagcgcggcg cggggcgggg cctgagtccc    120
tgtgagctgg aatctgagt gtgtgtgtgt gtgtgtgtgt gtgtgtgtgt gtgtgtgtgt      180
gtgtgtgtgt gtgtgagaga gagagagaga gagagagaga gagagagaga gagcgccatc    240
tgtgagcatt tagaatcctc tctatcctga gcaaggagtt ctgag                    285

<210> SEQ ID NO 139
<211> LENGTH: 273
<212> TYPE: DNA
<213> ORGANISM: Homo sapiens

<400> SEQUENCE: 139
cctggaagac aggcgggccg cggtggacac ctactgcaga cacaactacg gggttgtgga     60
gagcttcaca gtgcagtgca gcggcgaggt gagcgcggcg cggggcgggg cctgagtccc    120
tgtgagctgg aatctgagt gtgtgtgtgt gtgtgtgtgt gtgtgtgtgt gtgtgtgtgt      180
gtgtgtgaga gagagagaga gagagagaga gagagagagc gccatctgtg agcatttaga    240
atcctctcta tcctgagcaa ggagttctga gag                                273

<210> SEQ ID NO 140
<211> LENGTH: 225
<212> TYPE: DNA
<213> ORGANISM: Homo sapiens

<400> SEQUENCE: 140
cctggaggag aatcgggaca acggtggaca cctactgcag atacagttac ggggtttttg     60
agagcttcac agtgcagtgc agcgcctagg tgaacgcggc ggggggctgg gcctgagtcc    120
tgtgagctgg gaatttgagt ctgtgtgtgt gtgtgagaga gagagagaga gagaatctgt    180
gagcatttag aatcctctca atcctgagca aggagttctg aggag                   225

<210> SEQ ID NO 141
<211> LENGTH: 292
<212> TYPE: DNA
<213> ORGANISM: Macaca mulatta

<400> SEQUENCE: 141
cctggagcag aagcgggccc ggtggacaa ctactgcaga cacaactacg gggttttga       60 gagcttcaca gtgcagtgca gcggcgaggt gagcacggcg gggagaggga cctgggtccc    120
tgtgagctgg aatctgagt gtgtgtgtgt gtgtgtgtgt gtgtgtgtgt gtgagagaga     180
gagagagaaa gagagacaga gagagagaca gagagagaga cagagcgcgc gccatttgtg    240
agcatttaga atcctctcta tcctgaccaa ggagttctga gggcacaggt gt            292

<210> SEQ ID NO 142
<211> LENGTH: 295
<212> TYPE: DNA
<213> ORGANISM: Macaca mulatta

<400> SEQUENCE: 142
cctggagcag aagcgggccc aggtggacaa ctactgtaga cacaactacc gggttggtga     60
gagcttcaca gtgcagtgca gcggcgaggt gagcatggct gtggggaggg gggcctggat    120
ccctgtgagc tgggaatctg tgtgtgtgtg tgtgtgtgtg tgtgtgtgtg tgtgtgtgtg    180
tgagagagag agagagagag agagagagag agagagagag agagagagag agcgccgtct    240
gtgagcattc agaatcttct ctatcctgag caagcagttc tgagggcaca ggtgt         295
```

<210> SEQ ID NO 143
<211> LENGTH: 305
<212> TYPE: DNA
<213> ORGANISM: Macaca mulatta

<400> SEQUENCE: 143

| | |
|---|---|
| cctggagcag aagcggggcc gggtggacaa ctactgcaga tacaactatg ggggttgtgga | 60 |
| gagcttcaca gtgcagtgca gcggcgaggt gagcgcggcg ggggcggggc ctgggtccct | 120 |
| gtgagctggg aatctgagtg tgtgtgtgag tgtgtgtgag tgtgtgtgag tgtgtgtgtg | 180 |
| tgtgtgtgtg agtcagagag agagagagac acagacacag agagagagac agagacagag | 240 |
| cgcgccatct gtgatcattt agaatcttct ctatcctgac caagcagttt tgagggcaca | 300 |
| cgtgt | 305 |

<210> SEQ ID NO 144
<211> LENGTH: 267
<212> TYPE: DNA
<213> ORGANISM: Macaca mulatta

<400> SEQUENCE: 144

| | |
|---|---|
| cctggagcgg aggcgggccg aggtggacac agtgtgcaga cacaactacg ggggttgtgga | 60 |
| gagcttcaca gtgcagtgca gcggcgaggt gagcgcggcg ggggcggggc ctgggtccct | 120 |
| gtgagctggg aatctgagtg tgtgtgtgtg tgtgtgtgtg tgtgtgtgtg tgagagagag | 180 |
| agagagagag agagagagag agagcgccgt ctgtgagcat ttagaatcct ctctatcctg | 240 |
| agccagcagg tctgaggaca cagatgt | 267 |

<210> SEQ ID NO 145
<211> LENGTH: 237
<212> TYPE: DNA
<213> ORGANISM: Macaca mulatta

<400> SEQUENCE: 145

| | |
|---|---|
| cctggagcgg aggcgggccg aggtggacac agtgtgcaga cacaactacg ggttttttga | 60 |
| gagcttcaca gtgcagtgca gcggcgaggt gagcgcggcg ggggcgggac ctgggtccct | 120 |
| gtgagctggg aatctgagtg tgagaaagaa agagaaagaa agagagagag cgcgcgccat | 180 |
| ctgtgagcat ttagaatcct ctcaatcctg agcaaggagt tctgagggca caggtgt | 237 |

<210> SEQ ID NO 146
<211> LENGTH: 249
<212> TYPE: DNA
<213> ORGANISM: Macaca mulatta

<400> SEQUENCE: 146

| | |
|---|---|
| cctggaagac acgcgggccg cagtggacaa ctactgcaga tacaactacc ggattgcgga | 60 |
| gagcttcaca gtgcagtgca gcggcgaggt gagcgcgacg gggcctgggt ccctgtgagc | 120 |
| tgggaatctg tgtgtgtgtc tgtgtgtgtg tgtgtgtgtg tgtgagagag agagagagag | 180 |
| agagagagcc atctgtgagc atttagaatc ctctcaatcc cgagcaagca gttctgaggg | 240 |
| cacaggtgt | 249 |

<210> SEQ ID NO 147
<211> LENGTH: 255
<212> TYPE: DNA
<213> ORGANISM: Macaca mulatta

```
<400> SEQUENCE: 147
gtgagcgcgg cggggcggg gcctgggtcc ctgtgagctg ggaacctgag tgtgtgtgtg        60
agtgtgtgtg tgtgagagtg tgtgtgtgtg tgtgtgtgtg agtgtgagtg tgtgtatgtg       120
agagagagag agagagagag agagagagag agagagagag agagacagag acagagacag       180
agagagagcg cgcgccatct gtgggcattt agaatcctct ctatcctgag caaggagttc       240
tgagagcaca ggtgt                                                        255
```